(12) United States Patent
Surana et al.

(10) Patent No.: US 8,481,598 B2
(45) Date of Patent: Jul. 9, 2013

(54) STABLE DOSAGE FORMS OF LEVOMILNACIPRAN

(76) Inventors: Rahul Surana, Commack, NY (US); Murali Divi, Ronkonkoma, NY (US); Anil Chhettry, Holtsville, NY (US)

(*) Notice: Subject to any disclaimer, the term of this patent is extended or adjusted under 35 U.S.C. 154(b) by 114 days.

(21) Appl. No.: 13/006,993

(22) Filed: Jan. 14, 2011

(65) Prior Publication Data
US 2011/0144210 A1 Jun. 16, 2011

Related U.S. Application Data

(63) Continuation-in-part of application No. 12/941,293, filed on Nov. 8, 2010.

(60) Provisional application No. 61/294,898, filed on Jan. 14, 2010, provisional application No. 61/258,652, filed on Nov. 6, 2009.

(51) Int. Cl.
*A01N 37/18* (2006.01)
*A61K 31/165* (2006.01)
*C07C 233/00* (2006.01)
*C07C 235/00* (2006.01)
*C07C 237/00* (2006.01)
*C07C 239/00* (2006.01)

(52) U.S. Cl.
USPC ................ 514/620; 564/161; 564/190

(58) Field of Classification Search
USPC .................... 514/620; 564/161, 190
See application file for complete search history.

(56) References Cited

U.S. PATENT DOCUMENTS

| | | | |
|---|---|---|---|
| 5,532,244 A | 7/1996 | Wong et al. | |
| 6,028,070 A | 2/2000 | Heiligenstein | |
| 6,184,222 B1 | 2/2001 | Heiligenstein | |
| 6,602,911 B2 | 8/2003 | Kranzler et al. | |
| 6,635,675 B2 | 10/2003 | Kranzler et al. | |
| 6,699,506 B1 | 3/2004 | Paillard et al. | |
| 7,005,452 B2 | 2/2006 | Deregnaucourt et al. | |
| 7,074,833 B2 * | 7/2006 | Deregnaucourt et al. | 514/620 |
| 7,704,527 B2 | 4/2010 | Hirsh et al. | |
| 2002/0010216 A1 | 1/2002 | Rogosky et al. | |
| 2003/0130353 A1 | 7/2003 | Kranzler et al. | |
| 2003/0139476 A1 | 7/2003 | Kranzler et al. | |
| 2003/0203055 A1 | 10/2003 | Rao et al. | |
| 2003/0232805 A1 | 12/2003 | Kranzler et al. | |
| 2004/0019116 A1 | 1/2004 | Kranzler et al. | |
| 2004/0034101 A1 | 2/2004 | Rao et al. | |
| 2004/0122104 A1 | 6/2004 | Hirsh et al. | |
| 2004/0259953 A1 | 12/2004 | Deregnaucourt et al. | |
| 2005/0032782 A1 | 2/2005 | Rao et al. | |
| 2005/0096395 A1 | 5/2005 | Rao et al. | |
| 2006/0014837 A1 | 1/2006 | Deregnaucourt et al. | |
| 2006/0154938 A1 | 7/2006 | Kikuchi et al. | |
| 2009/0018203 A1 | 1/2009 | Hirsh et al. | |
| 2009/0049935 A1 | 2/2009 | Suzuki et al. | |
| 2011/0112197 A1 | 5/2011 | Dedhiya et al. | |
| 2011/0268720 A1 * | 11/2011 | Gruber et al. ............ | 424/94.6 |

FOREIGN PATENT DOCUMENTS

| | | |
|---|---|---|
| WO | 9735574 | 10/1997 |
| WO | 9808495 | 3/1998 |
| WO | 0162236 | 1/2001 |
| WO | 0126623 | 4/2001 |
| WO | 03068211 | 8/2003 |
| WO | 2004030633 | 4/2004 |
| WO | 2008104957 | 9/2008 |

OTHER PUBLICATIONS

Mansuy, L. "PO2-23 F2695: A new therapeutic potential for major depression. A Phase II Double-Blind Randomised Trial Results" European Psychiatry, Jan. 2009, vol. 24, supplement 1, p. S713, abstract.*
Food and Drug Administration "Bioavailability and bioequivalence studies for orally administered drug produts-General considerations" Oct. 2000, pp. 1-25.*
Kale et al. "Attempt to Desighn Continuous Dissolution—Absorption System Uising Everted Intestine Segment for In Vitro Absorption Studies of slow drug release formulations" Dissolution Technologies, May 2007, pp. 31-36.*
Retz, W. et al., Multiple and single dose pharmacokinetics of milnacipran in major depressive patients, FEBS Letters, vol. 5, No. 3, Sep. 1995, pp. 296-297(2).
Caron, et al., Acute electrophysiological effects of intravenous milnacipran, a new antidepressant agent, Eur Neuropsychopharmacol. Dec. 1993;3(4):493-500.
Mills, Serotonin Syndrome, A Clinical Update, Crit Care Clin. Oct. 1997;13(4):763-83.
Palazidou, et al., "Rapid Reference to Depression", Jul. 2002, 42-59.
Moret et al., Biochemical profile of midalcipran (F 2207), 1-phenyl-1-diethyl-aminocarbonyl-2-aminomethyl-cyclopropane (Z) hydrochloride, a potential fourth generation antidepressant drug 1985 Neuropharmacology 24(12): 1211-1219.
Grard et al., Enhancement of second-migrating enantiomer peak symmetry of basic drugs by using dual-cyclodextrin system in capillary electrophoresis Electrophorasis 2000 21: 3028-3034.
Doyle et al., A New Enantioselective Synthesis of Milnacipran and an Analogue by Catalytic Asymmetric Cyclopropanation 2001, Advanced Synthesis and Catalysis, vol. 343, 299-302.
Nores et al., Cardiovascular manifestations in acute poisoning by antidepressive agents. Discussion and review of the literature 1987 Therapie 42: 555-558.
Meador-Woodruff et al., Behavioral and cognitive toxicity related to elevated plasma tricyclic antidepressant levels J Clin Psychopharmacol. Feb. 1988;8(1):28-32.
The Diagnostic and Statistical Manual of Mental Disorders-IV(DSM-IV), 1995 A.P.A.
Deprez et al., Which bioequivalence study for a racemic drug? Application to milnacipran, Eur J Drug Metab Pharmacokinet. Apr.-Jun. 1998; 23(2): 166-71.
Spencer et al., Milnacipran. A review of its use in depression, Drugs. Sep. 1998;56(3):405-27.
Viazzo, et al., Microbiological ransformations 34: EnantioselectiveH ydrolysiso f a Key-Lactone Involved in the Synthesis of the Antidepressant Milnacipran®, Tetrahedron Letters, vol. 37, No. 26, pp. 4519-4522, 1996.
Shuto et al., Synthesis and biological activity of conformationally restricted analogues of milnacipran: (1S, 2R)-1-phenyl-2-[(R)-1-amino-2-propynyl]-N,N- diethylcyclopropanecarboxamide is a novel class of NMDA receptor channel blocker Journal of Medicinal Chemistry, 1998 vol. 41, pp. 3507-3514.

(Continued)

*Primary Examiner* — Kendra D Carter

(57) ABSTRACT

The present invention relates to stable dosage forms of levomilnacipran and pharmaceutically acceptable salts thereof. Processes for the preparation of these dosage forms and methods of using these dosage forms are also described.

8 Claims, 9 Drawing Sheets

OTHER PUBLICATIONS

Shuto et al., Synthesis and biological activity of conformationally restricted analogs of milnacipran: (1S,2R)-1-phenyl-2-[(S)-1-aminopropyl]-N,N-diethylcyclopropanecarboxami de, an efficient noncompetitive N-methyl-D-aspartic acid receptor antagonist.Journal of Med Chem, American Chem. Society, 1996, vol. 39: 4844-4852.

Shuto et al., (1S,2R)-1-Phenyl-2-[(S)-1-aminopropyl]-N,N-diethylcyclopropanecarboxamide (PPDC), a new class of NMDA-receptor antagonist: molecular design by a novel conformational restriction strategy, Jpn J Pharmacol. Mar. 2001;85(3):207-13.

Hindmarch I., The enantiomer debate: current status and future directions. Hum Psychopharmacol. Dec. 2001;16 (S2):S101-S104.

Baldwin D.S., Unmet needs in the pharmacological management of depression Hum Psychopharmacol. Dec. 2001;16(S2):S93-S99.

Artigas, "Selective Serotonin/Noradrenaline Reuptake Inhibitors", CNS Drugs, 1995, 4, 79-89.

Preskorn, et al., "Other Antidepressants", Antidepressants: Past, Present and Future, 2004, 264-311.

Preskorn, Milnacipran: A Dual Norepinephrine and Serotonin Reuptake Pump Inhibitor, Journal of Psychiatric Practice, 2004, 10, 119-126.

Yoshida, et al., Elevation of blood pressure induced by high-dose milnacipran, Hum. Psychopharmacol. Clin. Exp., 2002, 17, 431.

Ener, et al., "Serotonin Syndrome and Other Serotonergic Disorders", Pain Medicine, 2003, 4, 63-74.

Kolecki, "Isolated Venlafaxine-Induced Serotonin Syndrome", J. Emerg. Med., 1997, 15, 491-493.

Hansen, et al., "Long-term antidepressive medication—an increased anesthetic risk?", Der Anaesthesist, 1990, 39, 205-210 *Surgical Medline Extract).

Thase, "Effects of Venlafaxine on Blood Pressure: A Meta-Analysis of Original Data from 3744 Patients", J. Clin. Psychiatry, 1998, 59, 502-508.

Partridge, et al., "A Depressed Myocardium", Clinical Toxicology, 2000, 38, 453-455.

Jordan, et al., Influence of sibutramine on blood pressure: evidence from placebo-controlled trials, Int J Obes (Lond). May 2005;29(5):509-16.

Birkenfeld, et al., "Paradoxical effect of sibutramine of autonomic cardiovascular regulation", Circulation, 2002, 106, 2459-2465 (Medline Extract).

Sramek, et al., "Efficacy and safety of sibutramine for weight loss in obese patients with hypertension well controlled by beta-adrenergic blocking agents: a placebo-controlled, double-blind, radomiser trial", J. Hum. Hypertens., 2002, 16, 13-19 (Medline Extract).

Szabadi, et al., "The human pharmacology of reboxetine", Hum. Psychopharmacol., 1998, Suppl. 1, S3-S12 (Excerpta Medica Extract).

Middleton, et al., "Evidence that imipramine-induced postural hypotension may be centrally mediated", Hum. Psychopharmacol., 1998, 3, 181-190 (Excerpta Medica Extract).

Robinson, "Antidepressant Psychopharmacology: Current Limitations and Future Directions", Primary Psychiatry, 2003, 10, 43-49.

International Search Report for corresponding PCT/US2011/021315 mailed Mar. 23, 2011.

Written Opinion for corresponding PCT/US2011/021315 mailed Mar. 23, 2011.

* cited by examiner

US 8,481,598 B2

STABLE DOSAGE FORMS OF LEVOMILNACIPRAN

This application claims priority under 35 U.S.C. 119(e) to U.S. Provisional Application No. 61/294,898, filed on Jan. 14, 2010, and under 35 U.S.C. 120 as a continuation-in-part of U.S. patent application Ser. No. 12/941,293, filed on Nov. 8, 2010, which claims priority under 35 U.S.C. 119(e) to U.S. Provisional Application No. 61/258,652, filed on Nov. 6, 2009. The entire contents of these applications are incorporated herein by reference in their entirety.

FIELD OF THE INVENTION

The present invention relates to stable dosage formulations of levomilnacipran or a pharmaceutically acceptable salt thereof. Processes for the preparation of these dosage forms and methods of using these dosage forms are also described.

BACKGROUND OF THE INVENTION

Levomilnacipran is the international nonproprietary name for (1S,2R)-2-(amino methyl)-N,N-diethyl-1-phenyl cyclopropane carboxamide. It is a highly potent selective norepinephrine (NE) and serotonin (5-HT) reuptake inhibitor with greater selectivity for NE reuptake inhibition than for 5-HT reuptake inhibition. In particular, levomilnacipran has an inhibitory selectivity ratio for NE:5-HT of approximately 1.5:1. Accordingly, levomilnacipran is considered a norepinephrine-serotonin reuptake inhibitor (NSRI) that is pharmacologically distinct from serotonin-norepinephrine reuptake inhibitors (SNRI) having equal or higher inhibitory selectivity for 5-HT than for NE.

While formulations of levomilnacipran are generally discussed in the prior art, difficulties have been encountered in preparing stable dosage forms of levomilnacipran. These difficulties have arisen, at least in part, due to the sensitivity of levomilnacipran to certain reaction conditions and its reactivity with certain commonly-used excipients.

Accordingly, there is an existing and continual need for improved formulations of levomilnacipran having improved purity and stability. In addition, the improved-stability formulations must achieve a desirable pharmacokinetic profile that is associated with a low incidence of undesirable adverse events (for example, nausea, vomiting and gastric bleeding) in patients.

Improved formulations of levomilnacipran have now been discovered which achieve a desirable release of levomilnacipran upon entering a use environment and which have surprisingly high stability. These improved formulations of levomilnacipran are described herein.

SUMMARY OF THE INVENTION

The present invention relates to novel dosage forms of levomilnacipran, as well as processes for preparing these dosage forms and methods for using the dosage forms.

In some embodiments, the present invention relates to a stable dosage form that comprises levomilnacipran or a pharmaceutically acceptable salt thereof.

In some embodiments, the present invention relates to a stable dosage form that comprises, or consists essentially of, an active ingredient that comprises substantially pure levomilnacipran or a pharmaceutically acceptable salt thereof.

In some embodiments, the present invention relates to a stable dosage form that comprises, or consists essentially of, an active ingredient that comprises at least about 98% by weight (e.g., at least 98% by weight) of levomilnacipran or a pharmaceutically acceptable salt thereof.

In some embodiments, the present invention relates to a stable dosage form comprising levomilnacipran or a pharmaceutically acceptable salt thereof, wherein the dosage form comprises a X-ray powder diffraction (XRD) pattern that comprises characteristic peaks at 12.0, 20.1 and 22.5±0.2 degrees 2Ø. In some embodiments, the XRD pattern also comprises a characteristic peak at 32.7±0.2 degrees 2Ø. In some embodiments, the XRD pattern also comprises a characteristic peak at 32.7±0.2 degrees 2Ø. In some embodiments, the XRD pattern also comprises a characteristic peak at 6.0±0.2 degrees 2Ø.

In some embodiments, the present invention relates to a stable dosage form comprising levomilnacipran or a pharmaceutically acceptable salt thereof wherein the dosage form comprises a X-ray powder diffraction (XRD) pattern that comprises characteristic peaks at 6.0, 12.0 and 20.1±0.2 degrees 2Ø. In some embodiments, the XRD pattern also comprises a characteristic peak at 22.5±0.2 degrees 2Ø.

In some embodiments, the present invention relates to a stable dosage form comprising levomilnacipran or a pharmaceutically acceptable salt thereof and about 0.001% to about 0.5% by weight of (1S,5R) 1-phenyl-3-azabicyclo[3-1-0] hexane-2-one.

In some embodiments, the present invention relates to a stable dosage form comprising levomilnacipran or a pharmaceutically acceptable salt thereof and about 0.001% to about 0.2% by weight of (1S,5R) 1-phenyl-3-azabicyclo[3-1-0] hexane-2-one.

In some embodiments, the stable dosage form comprises about 45 wt. % to about 60 wt. % an active ingredient comprising substantially pure levomilnacipran or a pharmaceutically acceptable salt thereof.

In some embodiments, the stable dosage form comprises about 45 wt. % to about 60 wt. % an active ingredient comprising substantially pure levomilnacipran or a pharmaceutically acceptable salt thereof, and about 4 wt. % to about 10 wt. % of a binder.

In some embodiments, the stable dosage form comprises about 45 wt. % to about 60 wt. % an active ingredient comprising substantially pure levomilnacipran or a pharmaceutically acceptable salt thereof; about 30 wt. % to about 45 wt. % of an inert substrate or filler; and about 4 wt. % to about 10 wt. % of a binder.

In some embodiments, the stable dosage form comprises about 45 wt. % to about 60 wt. % an active ingredient comprising substantially pure levomilnacipran or a pharmaceutically acceptable salt thereof; about 30 wt. % to about 45 wt. % of an inert substrate or filler; about 4 wt. % to about 10 wt. % of a binder; and about 1 wt. % to about 5 wt. % of an anti-adherent or lubricant.

In some embodiments, the stable dosage form comprises about 50 wt. % to about 60 wt. % of levomilnacipran or a pharmaceutically acceptable salt thereof; about 30 wt. % to about 40 wt. % of an inert substrate or filler; about 4 wt. % to about 8 wt. % of a binder; and about 1 wt. % to about 5 wt. % of an anti-adherent or lubricant.

In some embodiments, the stable dosage form comprises about 40% to about 55% by weight of levomilnacipran or pharmaceutically acceptable salt thereof, about 5% to about 15% by weight of a release controlling agent, about 25% to about 40% by weight of an inert substrate, about 3% to about 10% by weight of a binder, about 3% to about 10% by weight of an anti-adherent, and about 0.1% to about 5% by weight of a plasticizer.

In some embodiments, the stable dosage form provides a dissolution rate of at least about 80% after about 6 hours to about 16 hours following entry into a use environment.

In some embodiments, the present invention relates to a stable oral dosage form comprising an active ingredient that comprises between about 10 mg and about 200 mg of levomilnacipran, wherein the dosage form comprises a X-ray powder diffraction (XRD) pattern that comprises characteristic peaks at 12.0, 20.1 and 22.5±0.2 degrees 2Ø.

In some embodiments, the present invention relates to an oral dosage form comprising between about 10 mg and about 200 mg of levomilnacipran and about 0.0001% to about 0.5% by weight (e.g., about 0.0001% to about 0.2% by weight or even about 0.0001% to about 0.1% by weight) of (1S,5R) 1-phenyl-3-azabicyclo[3-1-0]hexane-2-one.

In some embodiments, the present invention relates to an oral dosage form comprising between about 10 mg and about 200 mg of levomilnacipran and about 0.0001% to about 0.5% by weight (e.g., about 0.0001% to about 0.2% by weight or even about 0.0001% to about 0.1% by weight) of (1S,5R) 1-phenyl-3-azabicyclo[3-1-0]hexane-2-one, wherein the dosage form comprises a X-ray powder diffraction (XRD) pattern that comprises characteristic peaks at 12.0, 20.1 and 22.5±0.2 degrees 2Ø.

In some embodiments, the dosage form provides a dissolution rate of at least about 80% after about 6 hours to about 16 hours following entry into a use environment.

In some embodiments, the present invention relates to a stable dosage form comprising levomilnacipran or a pharmaceutically acceptable salt thereof and a release controlling agent, the dosage form sustaining release of the levomilnacipran or pharmaceutically acceptable salt thereof following entry of the dosage form into a use environment.

In some embodiments, the present invention relates to a stable oral dosage form comprising about 20 mg, about 40 mg, about 80 mg or about 120 mg of levomilnacipran or a pharmaceutically acceptable salt thereof.

In some embodiments, the present invention relates to a method for treating major depressive disorder comprising administering the stable dosage form of levomilnacipran or a pharmaceutically acceptable salt thereof to a patient in need thereof.

In some embodiments, the present invention relates to a method for treating major depressive disorder with concomitant fatigue comprising administering the stable dosage form of levomilnacipran or a pharmaceutically acceptable salt thereof to a patient in need thereof.

In some embodiments, the present invention relates to a method for preparing the stable dosage form, wherein the method comprises contacting an inert substrate with levomilnacipran or a pharmaceutically acceptable salt thereof and a dehydrated alcohol.

DETAILED DESCRIPTION OF THE INVENTION

Figure 1:
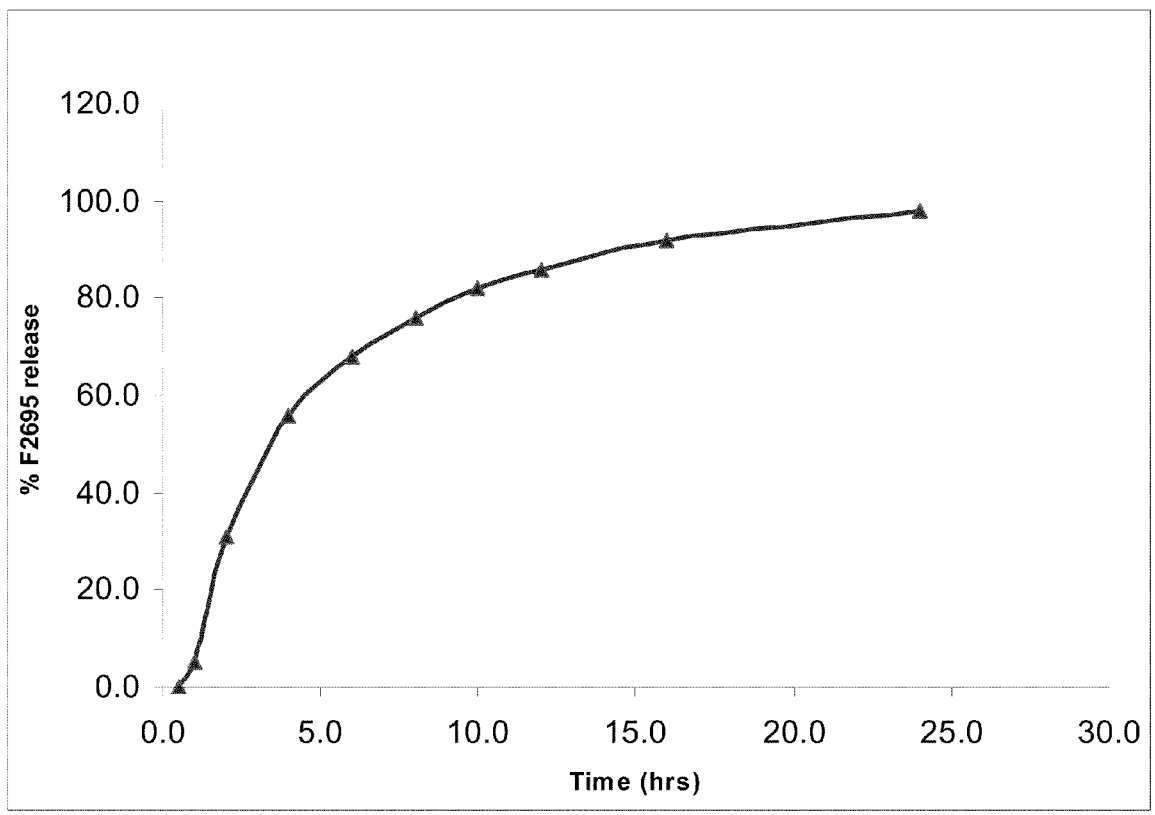
FIG. 1 shows the dissolution rates for a stable dosage form of levomilnacipran in accordance with an embodiment of the present invention.

Novel stable dosage forms of levomilnacipran, methods of treatment using these dosage forms, and methods for preparing these dosage forms are provided herein. The dosage forms of levomilnacipran have been found to achieve a desirable dissolution profile upon entering a use environment and to have surprisingly high stability.

DEFINITIONS

As used herein, the term "levomilnacipran" refers to (1S, 2R)-2-(amino methyl)-N,N-diethyl-1-phenyl cyclopropane carboxamide and pharmaceutically acceptable salts thereof. The term is not inclusive of other isomers of 2-(amino methyl)-N,N-diethyl-1-phenyl cyclopropane carboxamide (e.g., 1R,2S 2-(amino methyl)-N,N-diethyl-1-phenyl cyclopropane carboxamide) or degradants of (1S,2R)-2-(amino methyl)-N,N-diethyl-1-phenyl cyclopropane carboxamide (e.g., (1S,5R) 1-phenyl-3-azabicyclo[3-1-0]hexane-2-one). The term "pharmaceutically acceptable salt" refers to any salt of levomilnacipran that is physiologically tolerated by a patient (for example, levomilnacipran hydrochloride). The structural formula of levomilnacipran is shown below:

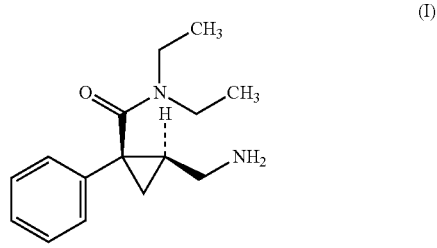 [SMILES: CCN(CC)C(=O)[C@]1(c2ccccc2)C[C@@H]1CN]

(I)

The term "substantially pure levomilnacipran" is used herein to mean at least 98% by weight of levomilnacipran. For example, an active pharmaceutical ingredient (i.e., active ingredient) that comprises substantially pure levomilnacipran comprises at least 98% by weight (e.g., about 98.5% by weight) of levomilnacipran and at most 2% by weight of total combined other components (such as other isomers of 2-(amino methyl)-N,N-diethyl-1-phenyl cyclopropane carboxamide and/or degradants of (1S,2R)-2-(amino methyl)-N,N-diethyl-1-phenyl cyclopropane carboxamide).

The term "stable", when used herein to refer to the dosage form means that the dosage form comprises an active ingredient that comprises substantially pure levomilnacipran.

The terms "dehydrated alcohol" and "dehydrated solvent" are defined herein as they are defined in the U.S. Pharmacopeia to mean an alcohol or solvent that contains less than or equal to 0.8% by weight of water, which corresponds to less or equal to 99.5% by volume of water. The term "dehydrated solvent" is used herein synonymously with the terms "substantially pure solvent," "anhydrous solvent," and "absolute solvent". Likewise, the term "dehydrated alcohol" is used herein synonymously with the terms "substantially pure alcohol," "anhydrous alcohol," and "absolute alcohol".

The term "treating" is used herein, unless otherwise indicated, to mean to relieve, alleviate, delay, reduce, reverse, improve or prevent at least one symptom of a disease, disorder or condition in a patient which may be treated by inhibition of norepinephrine (NE) and serotonin (5-HT) reuptake. The term "treating" may also mean to arrest, delay the onset (i.e., the period prior to clinical manifestation of a disease, disorder or condition) and/or reduce the risk of developing or worsening a disease, disease or condition which may be treated by inhibition of norepinephrine (NE) and serotonin (5-HT) reuptake.

The terms "dosage form" is used herein, unless otherwise indicated, to refer to any formulation of levomilnacipran that is suitable for oral administration to a human patient. For example, the term "dosage form" encompasses any oral dosage form or any solid oral dosage form, for example, compositions that are suitable for loading into capsules (e.g., beads, granules, microgranules, or the like), tablets, gelcaps, caplets, lozenges or powders). In some embodiments, the dosage form is a dosage form (e.g., bead, granule, microgranule or the like) that is suited for loading into capsules. In some embodiments, the dosage form is an immediate-release dosage form (e.g., an immediate-release solid dosage form, an immediate-release oral dosage form or an immediate-release solid oral dosage form).

In some embodiments, the dosage form is an immediate-release composition that is coated with a modified-release (e.g., sustained-release, delayed-release and/or extended release) composition. In some embodiments, the dosage form is a sustained-release dosage form (e.g., a sustained-release solid dosage form, a sustained-release oral dosage form, or a sustained-release solid oral dosage form). In some embodiments, the dosage form is a capsule (e.g., a bead-, granule- or microgranule-filled capsule). In some embodiments, the dosage form is a tablet. In some embodiments, the dosage form is a once-daily solid oral dosage form. In some embodiments, the dosage form is a once-daily capsule.

The term "sustained release" is used herein, unless otherwise indicated, to refer to dosage forms that release levomilnacipran (and optionally additional active agents contained therein) at a time other than promptly after administration, e.g., over an extended period of time that exceeds the duration of drug release from conventional instant- and immediate-release dosage forms of levomilnacipran.

The term "entry into a use environment" is used herein, unless otherwise indicated, to refer to contact of the stable dosage form of levomilnacipran with gastric or intestinal fluid of a patient to whom it is administered, with a fluid intended to simulate gastric or intestinal fluid, or with deionized water at a temperature of about 37° C. and subjected to USP apparatus II at 75 rpm (for example, with 1000 mL of deionized water at a temperature of about 37° C. and subjected to USP apparatus II at 75 rpm).

As used herein, unless otherwise indicated, dissolution rates define the percentage of levomilnacipran originally contained in an stable dosage form that is released from the dosage form within a specified period of time following entry of the dosage form into a use environment.

As used herein, unless otherwise indicated, the terms "effective amount" and "therapeutically effective amount" refer to an amount or quantity of levomilnacipran which is sufficient to elicit an appreciable biological response when administered to a patient. For example, the terms "effective amount" and "therapeutically effective amount" refer to an amount of levomilnacipran (or additional active agent contained in the dosage form) that, when administered to a patient (e.g., human or other mammal) for treating a disease, condition or disorder which may be treated by inhibition of norepinephrine (NE) and serotonin (5-HT) reuptake (e.g., major depressive disorder or anxiety), is sufficient to effect such treatment of one or more symptoms of the disease, disorder or condition, or an amount of levomilnacipran (or additional active agent contained in the dosage form) that is sufficient for inhibition of NE and 5-HT reuptake in a patient. It will be appreciated that the precise therapeutic dose will depend on the age, condition, weight, etc. of the patient and the nature of the condition being treated and will be ultimately be at the discretion of the attending physician.

For example, in some embodiments, the therapeutically effective dosage of levomilnacipran within the stable dosage form for treating depression (e.g., major depressive disorder) was found to be between about 10 mg and about 150 mg of an active ingredient comprising substantially pure levomilnacipran (e.g., between about 20 mg and about 120 mg of the active ingredient). In some embodiments, the dosage form comprises between about 15 mg and about 25 mg of an active ingredient comprising substantially pure levomilnacipran (e.g., about 20 mg). In some embodiments, the dosage form comprises between about 35 mg and about 45 mg of an active ingredient comprising substantially pure levomilnacipran (e.g., about 40 mg). In some embodiments, the dosage form comprises between about 70 mg and about 90 mg of an active ingredient comprising substantially pure levomilnacipran (e.g., about 80 mg). In some embodiments, the dosage form comprises between about 100 mg and about 140 mg of an active ingredient comprising substantially pure levomilnacipran (e.g., about 120 mg).

As used herein, unless otherwise indicated, the term "purity" when used in referring to the stable dosage forms means the degree to which the dosage form is free from (or lacks) specific undesirable components or impurities (for example, degradants or the like).

The term "consisting essentially of", when used in reference to the dosage form, means that the dosage form contains no additional active pharmaceutical ingredients but may contain additional inactive components or excipients.

As used herein, unless otherwise indicated, the terms "about" and "approximately" should be understood to mean within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value.

X-Ray Powder Diffraction Pattern of Oral Dosage Form

In some preferred embodiments, the stable dosage form, or the active ingredient contained within the dosage form, is crystalline in structure. In some preferred embodiments, the stable dosage form and the active ingredient contained within the dosage form are crystalline in structure. In some embodiments, the stable dosage form has an X-ray powder diffraction pattern (XRD) comprising one or more characteristic peaks as provided in Table 1. In some embodiments, the stable dosage form comprises an active ingredient comprising levomilnacipran wherein the active ingredient has an X-ray powder diffraction pattern (XRD) comprising one or more characteristic peaks as provided in Table 1.

As used herein, unless otherwise indicated, the phrase "one or more peaks" should be understood to be inclusive of (i) stable dosage forms that have XRD peaks at every peak value recited after this phrase, (ii) stable dosage forms that have an XRD peak at only one of the peak values recited after this phrase, as well (iii) stable dosage forms that have XRD peaks at two or more (e.g., three or more, four or more, five or more, six or more, or even seven or more) of the peak values recited after this phrase.

TABLE 1

| 2-Theta | d (Å) |
|---|---|
| 6.0 | 14.8 |
| 12.0 | 7.4 |
| 12.4 | 7.1 |
| 14.2 | 6.2 |
| 17.4 | 5.1 |
| 18.2 | 4.9 |
| 20.1 | 4.4 |
| 21.1 | 4.2 |
| 21.6 | 4.1 |
| 22.4 | 4.0 |
| 24.1 | 3.7 |
| 24.6 | 3.6 |
| 24.8 | 3.6 |
| 28.8 | 3.1 |
| 30.7 | 2.9 |
| 32.7 | 2.7 |
| 35.2 | 2.5 |

In some embodiments, the stable dosage form of levomilnacipran has an X-ray powder diffraction pattern (XRD) comprising one or more characteristic peaks as provided in Table 2.

TABLE 2

| 2-Theta | d (Å) |
|---|---|
| 2.3 | 39.2 |
| 5.9 | 14.9 |
| 9.5 | 9.3 |
| 11.9 | 7.4 |
| 12.3 | 7.2 |
| 14.1 | 6.3 |
| 16.5 | 5.4 |
| 17.3 | 5.1 |
| 18.1 | 4.9 |
| 20.0 | 4.4 |
| 21.7 | 4.1 |
| 22.4 | 4.0 |
| 24.5 | 3.6 |
| 28.6 | 3.1 |
| 30.6 | 2.9 |
| 32.7 | 2.7 |
| 34.5 | 2.6 |

In some embodiments, the stable dosage form of levomilnacipran is a modified-release dosage form (e.g., a sustain-release dosage form) and has an X-ray powder diffraction pattern (XRD) comprising one or more characteristic peaks as provided in Table 3.

TABLE 3

| 2-Theta | d (Å) |
|---|---|
| 6.0 | 14.7 |
| 8.3 | 10.6 |
| 9.6 | 9.2 |
| 12.0 | 7.4 |
| 12.8 | 6.9 |
| 13.1 | 6.7 |
| 14.2 | 6.2 |
| 15.6 | 5.7 |
| 16.4 | 5.4 |
| 16.8 | 5.3 |
| 17.4 | 5.1 |
| 18.3 | 4.8 |
| 18.9 | 4.7 |
| 19.6 | 4.5 |
| 20.0 | 4.4 |
| 20.4 | 4.4 |
| 20.9 | 4.2 |
| 21.6 | 4.1 |
| 22.1 | 4.0 |
| 22.5 | 4.0 |
| 23.6 | 3.8 |
| 24.7 | 3.6 |
| 25.2 | 3.5 |
| 26.4 | 3.4 |
| 27.5 | 3.2 |
| 28.7 | 3.1 |
| 30.6 | 2.9 |
| 31.0 | 2.9 |
| 32.0 | 2.8 |
| 32.7 | 2.7 |
| 33.5 | 2.7 |
| 34.6 | 2.6 |
| 36.2 | 2.5 |
| 37.3 | 2.4 |
| 38.3 | 2.3 |

In some embodiments, the present invention relates to a stable dosage form comprising levomilnacipran or a pharmaceutically acceptable salt thereof wherein the dosage form comprises a X-ray powder diffraction (XRD) pattern that comprises characteristic peaks at 12.0, 20.1 and 22.5±0.2 degrees 2Ø. In some embodiments, the XRD pattern also comprises a characteristic peak at 32.7±0.2 degrees 2Ø. In some embodiments, the XRD pattern also comprises a characteristic peak at 32.7±0.2 degrees 2Ø. In some embodiments, the XRD pattern also comprises a characteristic peak at 6.0±0.2 degrees 2Ø.

In some embodiments, the stable dosage form of levomilnacipran has an XRD comprising characteristic peaks at about 6.0, about 12.0 and about 20.1±0.2 degrees 2θ. In some embodiments, the stable dosage form has an XRD comprising characteristic peaks at about 6.0, about 12.0 and about 22.4±0.2 degrees 2θ. In some embodiments, the stable dosage form has an XRD comprising characteristic peaks at about 6.0, about 12.0, about 20.1 and about 22.4±0.2 degrees 2θ. In some embodiments, the stable dosage form has an XRD comprising characteristic peaks at about 6.0, about 20.1 and about 22.4±0.2 degrees 2θ. In some embodiments, the stable dosage form has an XRD comprising characteristic peaks at about 12.0, about 20.1 and about 22.4±0.2 degrees 2θ. In some embodiments, the stable dosage form has an XRD comprising characteristic peaks at about 6.0 and about 12.0±0.2 degrees 2θ. In some embodiments, the stable dosage form has an XRD comprising characteristic peaks at about 6.0 and about 20.1±0.2 degrees 2θ. In some embodiments, the stable dosage form has an XRD comprising characteristic peaks at about 6.0 and about 22.4±0.2 degrees 2θ.

In some embodiments, the stable dosage form has an XRD comprising characteristic peaks at about 12.0 and about 20.1±0.2 degrees 2θ. In some embodiments, the stable dosage form has an XRD comprising characteristic peaks at about 12.0 and about 22.4±0.2 degrees 2θ. In some embodiments, the stable dosage form has an XRD comprising characteristic peaks at about 20.1±0.2 degrees 2θ and at about 22.4±0.2 degrees 2θ. In some embodiments, the stable dosage form comprises a crystalline form of levomilnacipran having an XRD that comprises characteristic peaks at one or more of about 6.0±0.2 degrees 2θ, about 12.0±0.2 degrees 2θ, about 20.1±0.2 degrees 2θ and about 22.4±0.2 degrees 2θ.

In some embodiments, the stable dosage form comprises an active ingredient that comprises substantially pure levomilnacipran wherein the active ingredient comprises one or more of the characteristic peaks shown in Table 1. In some embodiments, the stable dosage form comprises an active ingredient that comprises substantially pure levomilnacipran wherein the stable dosage form comprises one or more of the characteristic peaks shown in Table 1 or Table 2.

Purity of the Stable Dosage Forms

The stable dosage form and the active ingredient in the dosage form have been found to comprise a surprisingly low concentration of (1S,5R) 1-phenyl-3-azabicyclo[3-1-0]hexane-2-one, which is represented by Formula (II):

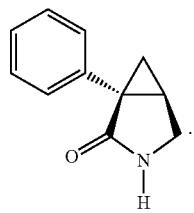

(II)

In some embodiments, the stable dosage form comprises about 0.0001 to about 0.2% by weight of (1S,5R) 1-phenyl-3-azabicyclo[3-1-0]hexane-2-one, as defined by the International Conference on Harmonization (ICH) guidelines, for example after storage for one, two or three months of storage at 40° C. and 75% relative humidity. In some embodiments, the stable dosage form comprises less than about 0.2% by weight of (1S,5R) 1-phenyl-3-azabicyclo[3-1-0]hexane-2-one, for example after storage for one, two or three months of storage at 40° C. and 75% relative humidity. In some embodiments, the stable dosage form comprises about 0.0001 to about 0.1% by weight of (1S,5R) 1-phenyl-3-azabicyclo[3-1-0]hexane-2-one, for example, after storage for one, two or three months of storage at 40° C. and 75% relative humidity.

In some preferred embodiments, the stable dosage form comprises about 0.001 to about 0.2 wt. %, about 0.01 to about 0.2 wt. %, about 0.0001 to about 0.15 wt. %, about 0.001 to about 0.15 wt. %, about 0.01 to about 0.15 wt. %, about 0.001 to about 0.1 wt. %, about 0.01 to about 0.1 wt. %, about 0.01 to about 0.08 wt. %, or even about 0.001 to about 0.08 wt. % of (1S,5R) 1-phenyl-3-azabicyclo[3-1-0]hexane-2-one, for example, after storage for one, two, three, four, five or six months of storage at 40° C. and 75% relative humidity. In some embodiments, the stable dosage form comprises about 0.01 to about 0.08 wt. % (e.g., about 0.001 to about 0.08 wt. %) of (1S,5R) 1-phenyl-3-azabicyclo[3-1-0]hexane-2-one, for example, after storage for one, two, three, four, five or six months of storage at 40° C. and 75% relative humidity.

Preparation of the Stable Dosage Form

The stable dosage forms of levomilnacipran can be prepared by any suitable process. In some preferred embodiments, the stable dosage forms are prepared by a method comprising contacting an inert substrate or filler with a solution that comprises (or consists essentially of or consists of) levomilnacipran, a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water) (e.g., a dehydrated alcohol such as 200-proof ethanol) and optionally a binder and an anti-adherent or lubricant, to form a levomilnacipran composition. In some embodiments, the dosage forms of levomilnacipran are then coated to render them sustained-release dosage forms by contacting the levomilnacipran composition with a solution that comprises a release controlling agent, a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water) (e.g., a dehydrated alcohol such as 200-proof ethanol) and optionally a plasticizer, an anti-adherent or glidant.

In some preferred embodiments, the stable dosage forms are prepared by a method comprising contacting an inert substrate or filler with a solution that comprises levomilnacipran, a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water), a binder, and an anti-adherent or lubricant, to form a levomilnacipran composition. In some embodiments, the dosage forms of levomilnacipran are then coated to render them sustained-release dosage forms by contacting the levomilnacipran composition with a solution that comprises a release controlling agent, a plasticizer, an anti-adherent or glidant, and a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water).

In some embodiments, the stable dosage forms are prepared by a method comprising contacting an inert substrate or filler with levomilnacipran and optionally a binder, an anti-adherent or lubricant, and/or a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water) to form a levomilnacipran composition (e.g., a levomilnacipran core or levomilnacipran beads or granules). In some embodiments, the dosage forms of levomilnacipran are then coated to render them sustained-release dosage forms by contacting the levomilnacipran composition with a release controlling agent and optionally a plasticizer, an anti-adherent or lubricant; and/or a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water).

In some embodiments, the stable dosage forms are prepared by a method comprising contacting an inert substrate or filler with a solution that comprises levomilnacipran, a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water) and optionally a binder and an anti-adherent (or lubricant) to form a levomilnacipran composition (e.g., a core, bead or granule comprising levomilnacipran). In some embodiments, the method further comprises coating the levomilnacipran composition with a solution that comprises (or consists essentially of or consists of) a release controlling agent and optionally a plasticizer, an anti-adherent or lubricant; and/or a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water).

In some embodiments, the stable dosage forms are prepared by a method comprising contacting an inert substrate or filler with a solution comprising levomilnacipran, a binder, an anti-adherent or lubricant, and a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water). In some embodiments, the contacting step comprises layering the inert substrate with a drug layering solution that consists essentially of levomilnacipran, a binder, an anti-adherent (or lubricant) and a solvent (e.g., a solvent comprising less than 5 wt. %, less than 4 wt. %, less than 3 wt. %, less than 2 wt. %, less than 1 wt. %, less than 0.8 wt. %, less than 0.5 wt. %, or even less than 0.1 wt. % of water).

In some preferred embodiments, the contacting step (e.g., drug layering step) is performed by a Wurster process (e.g., within a Wurster apparatus) or the like. In some preferred embodiments, the coating step is performed by a Wurster process (e.g., within a Wurster apparatus) or the like. In some preferred embodiments, the combining step and the contacting steps are both performed by a Wurster process or the like.

The process for determining the relative percentages of levomilnacipran and other isomers of 2-(amino methyl)-N,N-diethyl-1-phenyl cyclopropane carboxamide (e.g., 1R,2S 2-(amino methyl)-N,N-diethyl-1-phenyl cyclopropane carboxamide) in the active pharmaceutical ingredient can be performed using any suitable method, preferably by reverse phase high performance liquid chromatograph (RP HPLC) (for example, with a UV detection at 220 nm).

Components of the Stable Dosage Forms

The stable dosage form can comprise any therapeutically effective amount of levomilnacipran. In some embodiments, the stable dosage form comprises about 5 to about 200 mg of levomilnacipran. In some embodiments, the stable dosage form comprises about 10 to about 180 mg of levomilnacipran. In some embodiments, the stable dosage form comprises about 20 to about 150 mg of levomilnacipran. In some embodiments, the stable dosage form comprises about 20 to about 120 mg of levomilnacipran. For example, the stable dosage form can comprise about 20 mg, about 40 mg, about 50 mg, about 60 mg, about 80 mg, about 100 mg, 120 mg, or about 240 mg of levomilnacipran. In this regard, the stable dosage form can comprise any suitable weight percentage of levomilnacipran relative to other components of the dosage form. For example, the stable dosage form can comprise about 35 to about 65% by weight (e.g., about 35 to about 60 wt. %, about 35 to about 55 wt. %, about 40 to about 55 wt. %, or about 40 to about 50 wt. %) of levomilnacipran.

The stable dosage form of levomilnacipran also comprises an inert substrate or filler. In some preferred embodiments, the stable dosage form comprises an inert substrate that comprises sugar for example sucrose (e.g., sugar spheres). Other suitable inert substrates or fillers include, for example, isomalt, dicalcium phosphate dihydrate, calcium sulfate, lactose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate, or a mixture thereof.

The stable dosage form can comprise any suitable amount of the inert substrate or filler (e.g., sugar spheres). In some embodiments, the stable dosage form comprises about 15 to about 45% by weight of the inert substrate or filler. In some embodiments, the stable dosage form comprises about 20 to about 40 wt. % of the inert substrate or filler. In some embodiments, the stable dosage form comprises about 25 to about 40 wt. % of the inert substrate or filler. In some embodiments, the stable dosage form comprises about 30 to about 40 wt. % of the inert substrate or filler In some embodiments, the stable dosage form comprises about 35 to about 40 wt. % of the inert substrate or filler.

The stable dosage form can comprise sugar spheres in any suitable size. In some embodiments, the stable dosage form comprises sugar spheres having a size of about 20 to about 50 mesh. In some embodiments, the stable dosage form comprises sugar spheres having a size of approximately about 25 to about 45 mesh. In some embodiments, the stable dosage form comprises sugar spheres having a size of about 25 to about 40 mesh. In some preferred embodiments, the stable dosage form comprises sugar spheres having a size of approximately about 30 to about 40 mesh (for example, about 30 to about 35 mesh). For example, the stable dosage form may comprise about 30 to about 40 wt. % (e.g., about 35 to about 40 wt. %) of sugar spheres having a size of about 30 to about 40 mesh.

The stable dosage form also comprises a binder in some preferred embodiments, for example polyvinyl pyrrolidone (e.g., Povidone K30). Other suitable binders include, for example, starch, polyvinyl alcohol, pre-gelatinized starch, gelatin, sucrose, glucose, dextrose, lactose, sorbitol, polyethylene glycol, waxes, natural and synthetic gums such as acacia, tragacanth, sodium alginate, hydroxypropylmethylcellulose, hydroxypropylcellulose, ethylcellulose, veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid, or a mixture thereof.

The stable dosage form can comprise any suitable amount of the binder (e.g., PVP). In some embodiments, the stable dosage form comprises about 0.1 to about 15% by weight of a binder. In some embodiments, the stable dosage form comprises about 1 to about 12% by weight of a binder. In some embodiments, the stable dosage form comprises about 1 to about 10% by weight of a binder. In some embodiments, the stable dosage form comprises about 2 to about 10% by weight of a binder.

In some preferred embodiments, the stable dosage form comprises about 3 to about 10% by weight of a binder (e.g., PVP). In some embodiments, the stable dosage form comprises about 4 to about 10% by weight of the binder. In some embodiments, the stable dosage form comprises about 2 to about 8% by weight of the binder. In some embodiments, the stable dosage form comprises about 4 to about 8% by weight of the binder. In some embodiments, the stable dosage form comprises about 5 to about 7% by weight of the binder.

The stable dosage form also comprises an anti-adherent or lubricant in some preferred embodiments, for example, talc. Other suitable anti-adherents or lubricants include, for example, magnesium stearate, calcium stearate, stearic acid, glycerol behenate, polyethylene glycol, talc, mineral oil, sodium stearyl fumarate or mixtures thereof.

The stable dosage form can comprise any suitable amount of the lubricant or anti-adherent (for example, talc). In some embodiments, the stable dosage form comprises about 0.1 to about 15% by weight of the lubricant or anti-adherent. In some embodiments, the stable dosage form comprises about 1 to about 12% by weight of the lubricant or anti-adherent. In some embodiments, the stable dosage form comprises about 2 to about 10% by weight of the lubricant or anti-adherent. In some embodiments, the stable dosage form comprises about 3 to about 10% by weight of the lubricant or anti-adherent. In some embodiments, the stable dosage form comprises about 4 to about 10% by weight of the lubricant or anti-adherent. In some embodiments, the stable dosage form comprises about 4 to about 8% by weight of the lubricant or anti-adherent. In some embodiments, the stable dosage form comprises about 5 to about 8% by weight of the lubricant or anti-adherent.

In some preferred embodiments, the stable dosage form comprises about 4 to about 7.5% by weight of the lubricant or anti-adherent. In some preferred embodiments, the stable dosage form comprises about 5 to about 7% by weight of the lubricant or anti-adherent.

In some embodiments, the stable dosage form is a sustained-release (SR) dosage form and comprises a release controlling agent, polymeric agent or coating polymer (e.g., ethyl cellulose) which substantially contributes to sustaining the release of levomilnacipran from the dosage form. Other suitable release controlling agents include, for example, a cellulose and cellulose derivative, wax, carbomer, polyalkylene polyol, polycarbophil, methacrylic acid derivative, gelatin, gum, polyethylene oxide, and polyvinyl pyrrolidone, or mixtures thereof. In some embodiments, the release controlling agent, polymeric additive or coating polymer is selected from ethyl cellulose, hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, cellulose acetate, cellulose acetate phthalate, cellulose acetate trimellitate and carboxymethylcellulose sodium; acrylic acid polymers and copolymers (preferably formed from acrylic acid, methacrylic acid, methyl acrylate, ethyl acrylate, methyl methacrylate and/or ethyl methacrylate), and other methacrylic resins that are commercially available under the trade name Eudragit™ (Rohm Pharma; Westerstadt, Germany), including Eudragit™ L30D-55 and L100-55, Eudragit™, Eudragit™ and Eudragit™ NE, RL and RS; vinyl polymers and copolymers such as polyvinyl pyrrolidone, vinyl acetate, vinyl acetate phthalate, vinyl acetate crotonic acid copolymer, and ethylene-vinyl acetate copolymer; enzymatically degradable polymers such as azo polymers, pectin, chitosan, amylose and guar gum; zein and shellac, or mixtures thereof.

The stable dosage form can comprise any suitable amount of the release controlling agent, polymeric agent or coating polymer (e.g., ethyl cellulose). The stable dosage form preferably comprises about 5 to about 15% by weight of the release controlling agent, polymeric agent or coating polymer. However, n some embodiments, the stable dosage form comprises about 2 to about 20% by weight of a release controlling agent, polymeric agent or coating polymer. In some embodiments, the stable dosage form comprises about 5 to about 12% by weight of a release controlling agent, polymeric agent or coating polymer. In some embodiments, the stable dosage form comprises about 8 to about 12% by weight of a release controlling agent, polymeric agent or coating polymer. In some embodiments, the stable dosage form comprises about 8 to about 11% by weight of a release controlling agent, polymeric agent or coating polymer. In some embodiments, the stable dosage form comprises about 8 to about 10% by weight of a release controlling agent, polymeric agent or coating polymer.

The stable dosage form also comprises a plasticizer in some preferred embodiments, for example triethyl citrate. Other suitable plasticizers include, for example, polyethylene glycol, propylene glycol, triacetin, dimethyl phthalate, diethyl phthalate, dibutyl phthalate, dibutyl sebacate, tributyl citrate, triethyl acetyl citrate, glycerol monostearate, castor oil, acetylated monoglycerides, or a mixture thereof.

The stable dosage form can comprise any suitable amount of the plasticizer (for example, triethyl citrate). In some embodiments, the stable dosage form comprises about 0.1 to about 10% by weight of the plasticizer. In some embodiments, the stable dosage form comprises about 0.5 to about 8% by weight of the plasticizer. In some embodiments, the stable dosage form comprises about 0.5 to about 5% by weight of the plasticizer. In some embodiments, the stable dosage form comprises about 1 to about 5% by weight of the plasticizer. In some embodiments, the stable dosage form comprises about 1 to about 3% by weight of the plasticizer.

In addition, the stable dosage form of levomilnacipran can comprise any additional excipients or additives in some embodiments, such as plasticizers, pigments, colorants, stabilizing agents, glidants, or the like.

In some preferred embodiments, the dosage form comprises about 30 wt. % to about 65 wt. % (e.g., about 40 wt. % to about 60 wt. %, about 45 wt. % to about 60 wt. % or even about 50 wt. % to about 60 wt. %) of levomilnacipran (or an active ingredient comprising at least 98% by weight or even substantially pure levomilnacipran); about 25 wt. % to about 55 wt. % (e.g., about 30 wt. % to about 45 wt. % or even about 30 wt. % to about 40 wt. %) of an inert substrate or filler; about 2 wt. % to about 12 wt. % (e.g., about 4 wt. % to about 10 wt. % or even about 4 wt. % to about 8 wt. %) of a binder; and about 0.5 wt. % to about 10 wt. % (e.g., about 1 wt. % to about 8 wt. %, about 1 wt. % to about 5 wt. % or even about 2 wt. % to about 5 wt. %) of an anti-adherent or lubricant.

In some preferred embodiments, the dosage form comprises about 45 wt. % to about 60 wt. % of levomilnacipran (or an active ingredient comprising at least 98% by weight or even substantially pure levomilnacipran); about 30 wt. % to about 45 wt. % of an inert substrate or filler; about 4 wt. % to about 10 wt. % of a binder; and about 1 wt. % to about 5 wt. % of an anti-adherent or lubricant.

In some preferred embodiments, the dosage form comprises about 50 wt. % to about 60 wt. % of levomilnacipran (or an active ingredient comprising at least 98% by weight or even substantially pure levomilnacipran); about 30 wt. % to about 40 wt. % of an inert substrate or filler; about 4 wt. % to about 8 wt. % of a binder; and about 1 wt. % to about 5 wt. % of an anti-adherent or lubricant.

In some preferred embodiments, the stable dosage form comprises 40 to about 55 wt. % (e.g., about 40 to about 50 wt. %) of levomilnacipran; about 3 to about 10 wt. % (e.g., about 4 to about 8 wt. %) of a binder (e.g., PVP); and about 0.1 to about 4 wt. % (e.g., about 1 to about 3 wt. %) of a plasticizer (e.g., triethyl citrate).

In some preferred embodiments, the stable dosage form comprises 40 to about 55 wt. % (e.g., about 40 to about 50 wt. %) of levomilnacipran; about 3 to about 7 wt. % (e.g., about 4 to about 7 wt. %) of an anti-adherent or lubricant (for example, talc); and about 0.1 to about 4 wt. % (e.g., about 1 to about 3 wt. %) of a plasticizer (e.g., triethyl citrate).

In some preferred embodiments, the stable dosage form comprises 40 to about 55 wt. % (e.g., about 40 to about 50 wt. %) of levomilnacipran; about 3 to about 10 wt. % (e.g., about 4 to about 8 wt. %) of a binder (e.g., PVP); about 3 to about 7 wt. % (e.g., about 4 to about 7 wt. %) of an anti-adherent or lubricant (for example, talc); and about 0.1 to about 4 wt. % (e.g., about 1 to about 3 wt. %) of a plasticizer (e.g., triethyl citrate).

In some preferred embodiments, the stable dosage form comprises 40 to about 55 wt. % (e.g., about 40 to about 50 wt.

%) of levomilnacipran; about 3 to about 10 wt. % (e.g., about 4 to about 8 wt. %) of a binder (e.g., PVP); and about 5-10.5% by weight (e.g., about 6 to about 10 wt. %) of a release controlling agent (for example, ethyl cellulose).

In some preferred embodiments, the stable dosage form comprises 40 to about 55 wt. % (e.g., about 40 to about 50 wt. %) of levomilnacipran; about 3 to about 7 wt. % (e.g., about 4 to about 7 wt. %) of an anti-adherent or lubricant (for example, talc); and about 5-10.5% by weight (e.g., about 6 to about 10 wt. %) of a release controlling agent (for example, ethyl cellulose).

In some preferred embodiments, the stable dosage form comprises 40 to about 55 wt. % (e.g., about 40 to about 50 wt. %) of levomilnacipran; about 3 to about 10 wt. % (e.g., about 4 to about 8 wt. %) of a binder (e.g., PVP); about 5-10.5% by weight (e.g., about 6 to about 10 wt. %) of a release controlling agent (for example, ethyl cellulose); and about 5-10.5% by weight (e.g., about 6 to about 10 wt. %) of a release controlling agent (for example, ethyl cellulose).

In some preferred embodiments, the stable dosage form comprises 40 to about 55 wt. % (e.g., about 40 to about 50 wt. %) of levomilnacipran; about 3 to about 7 wt. % (e.g., about 4 to about 7 wt. %) of an anti-adherent or lubricant (for example, talc); about 5-10.5% by weight (e.g., about 6 to about 10 wt. %) of a release controlling agent (for example, ethyl cellulose); and about 5-10.5% by weight (e.g., about 6 to about 10 wt. %) of a release controlling agent (for example, ethyl cellulose).

In some preferred embodiments, the stable dosage form comprises about 35 to about 60% by weight (e.g., about 35 to about 55 wt. % or about 40 to about 55 wt. %) of levomilnacipran; about 20 to about 45% by weight (e.g., about 20 to about 40 wt. %, about 25 to about 40 wt. % or about 25 to 35 wt. %) of an inert substrate or filler (e.g., sugar spheres); about 1 to about 15% by weight (e.g., about 2 to about 12 wt. %, about 3 to about 10 wt. %, about 3 to about 9 wt. % or about 4 to about 8 wt. %) of a binder (for example, PVP); about 1 to about 15% by weight (e.g., about 2 to about 12 wt. %, about 3 to about 10 wt. %, about 3 to about 9 wt. %, about 4 to about 8 wt. % or about 4 to about 7 wt. %) of an anti-adherent or lubricant (for example, talc); about 1-20% by weight (e.g., about 5 to about 15 wt. % or about 8 to about 12 wt. %) of a release controlling agent (for example, ethyl cellulose); and about 0.1 to about 10% by weight (e.g., about 0.1 to about 5 wt. % or about 1 to about 5 wt. % or about 1 to about 3 wt. %) of a plasticizer (for example, triethyl citrate).

In some preferred embodiments, the stable dosage form comprises about 35 to about 60% by weight (e.g., about 35 to about 55 wt. % or about 40 to about 55 wt. %) of levomilnacipran; about 20 to about 45% by weight (e.g., about 20 to about 40 wt. %, about 25 to about 40 wt. % or about 25 to 35 wt. %) of an inert substrate (e.g., sugar substrate) (e.g., about 30-35 mesh sugar spheres); about 1 to about 15% by weight (e.g., about 2 to about 12 wt. %, about 3 to about 10 wt. %, about 3 to about 9 wt. % or about 4 to about 8 wt. %) of PVP (e.g., Povidone K30); about 1 to about 15% by weight (e.g., about 2 to about 12 wt. %, about 3 to about 10 wt. %, about 3 to about 9 wt. %, about 3 to about 8 wt. %, about 4 to about 8 wt. % or about 4 to about 7 wt. %) of talc; about 1-20% by weight (e.g., about 5 to about 15 wt. % or about 8 to about 12 wt. %) of ethyl cellulose; and about 0.1 to about 10% by weight (e.g., about 0.1 to about 5 wt. % or about 1 to about 5 wt. % or about 1 to about 3 wt. %) of triethyl citrate.

In some preferred embodiments, the stable dosage form comprises 40 to about 55 wt. % (e.g., about 40 to about 50 wt. %) of levomilnacipran; about 25 to about 40 wt. % of sugar spheres (e.g., about 30-35 mesh sugar spheres); about 2 to about 10 wt. % (e.g., about 4 to about 8 wt. %) of PVP (e.g., Povidone K30); about 2 to about 10 wt. % (e.g., about 4 to about 8 wt. %) of talc; about 5 to about 15 wt. % of ethyl cellulose; about 0.1 to about 5 wt. % (e.g., about 1 to about 5 wt. %) of triethyl citrate.

The stable dosage forms can comprise beads or granules (e.g., microgranules or other like core) of levomilnacipran that are coated with release controlling agent in any suitable thickness to achieve a desired pK profile. In some embodiments, for example, the stable dosage form is a capsule that contains beads or granules (or similar core), wherein the beads or granules (or similar core) are coated with a coating composition comprising a release controlling agent (and optionally a plasticizer, anti-adherent or lubricant, and/or a solvent) having any desired average thickness. For example, the coating composition can be applied to the beads or granules (or similar core) with an average thickness of about 1 to about 100 microns (e.g., about 5 to about 75 microns, about 5 to about 60 microns, about 5 to about 50 microns, about 5 to about 40 microns, about 5 to about 30 microns, about 10 to about 30 microns, about 15 to about 30 microns, about 20 to about 30 microns, about 25 to about 35 microns, or even about 25 to about 35 microns).

In some preferred embodiments, for example, the stable dosage form comprises coated beads or granules (or similar core) of levomilnacipran wherein the coating comprises one or more release controlling agents (e.g., ethyl cellulose) and wherein the average thickness of the coating on the beads or granules (or similar core) is about 20 to about 35 microns (e.g., about 20 to about 30 microns). For example, the dosage form can be a bead-, granule- or microgranule-filled capsule wherein the beads, granules or microgranules (or similar core) are coated with a coating composition (e.g., comprising ethyl cellulose) at an average thickness of about 20 to about 30 microns (e.g., approximately 25 microns).

In some embodiments, the stable dosage form is in the form of beads or granules (e.g., coated beads or granules) which have an average diameter of about 400 to about 900 microns. In some embodiments, the stable dosage form is in the form of beads or granules (e.g., coated beads or granules) which have an average diameter of about 500 to about 800 microns. In some embodiments, the stable dosage form is in the form of beads or granules (e.g., coated beads or granules) which have an average diameter of about 600 to about 800 microns. In some embodiments, the stable dosage form is in the form of beads or granules (e.g., coated beads or granules) which have an average diameter of about 600 to about 750 microns. In some embodiments, the stable dosage form is in the form of beads or granules (e.g., coated beads or granules) which have an average diameter of about 650 to about 850 microns. In some embodiments, the stable dosage form is in the form of beads or granules (e.g., coated beads or granules) which have an average diameter of less than about 1000 microns. In some embodiments, the stable dosage form is in the form of beads or granules (e.g., coated beads or granules) which have an average diameter of less than about 900 microns.

The invention also provides a method for using the stable dosage form of levomilnacipran in the manufacture of a medicament for the treatment of a disorder that can be managed by inhibition of 5-HT and NE reuptake, for example, anxiety disorders or depression (e.g., major depressive disorder).

In some embodiments, the stable dosage form is loaded into a capsule (e.g., an HPMC or gelatin capsule). For example, in some preferred embodiments, the stable dosage form is loaded into an HPMC capsule. Such an HPMC capsule can then be packaged in bottles or canisters with or without a desiccant (e.g., about 0.01 to about 2 grams, about 0.01 to about 1 gram or even about 0.01 to about 0.8 grams of desiccant). In some preferred embodiments, the stable dosage form is contained within HPMC capsules and packaged without a desiccant. In some preferred embodiments, the stable dosage form is contained within HPMC capsules and packaged with a desiccant. In some embodiments, the stable dosage form is contained within gelatin capsules and packaged without a desiccant. In some embodiments, the stable dosage form is contained within gelatin capsules and packaged with a desiccant.

Dissolution Rate of the Stable Dosage Forms

The stable dosage forms of levomilnacipran have been found to provide desirable dissolution rates following entry into a use environment. In some embodiments, the stable dosage form provides a dissolution rate (e.g., a single phase dissolution rate) of at least about 80% (e.g., at least 80%) after about 6 hours to about 16 hours following entry into a use environment. In some embodiments, the stable dosage form provides a dissolution rate of at least about 80% after about 6 hours to about 12 hours following entry into a use environment.

In some embodiments, the stable dosage form provides a dissolution rate (e.g., a single phase dissolution rate) of less than about 60% after about 2 hours following entry into a use environment. In some embodiments, the stable dosage form provides a dissolution rate (e.g., a single phase dissolution rate) of less than about 55% after about 2 hours following entry into a use environment. In some embodiments, the stable dosage form provides a dissolution rate of less than about 50% after about 2 hours following entry into a use environment. In some embodiments, the stable dosage form provides a dissolution rate of less than about 45% after about 2 hours following entry into a use environment. In some embodiments, the stable dosage form provides a dissolution rate of less than about 40% after about 2 hours following entry into a use environment. In some embodiments, the stable dosage form provides a dissolution rate of about 20% to about 60% after about 2 hours following entry into a use environment. In some embodiments, the stable dosage form provides a dissolution rate of about 25% to about 55% after about 2 hours following entry into a use environment. In some embodiments, the stable dosage form provides a dissolution rate of about 30% to about 50% after about 2 hours following entry into a use environment.

In some embodiments, the stable dosage form provides a dissolution rate (e.g., a single phase dissolution rate) of less than about 90% after about 4 hours following entry into a use environment. In some embodiments, the stable dosage form provides a dissolution rate of less than about 80% after about 4 hours following entry into a use environment. In some embodiments, the stable dosage form provides a dissolution rate of less than about 70% after about 4 hours following entry into a use environment. In some embodiments, the stable dosage form provides a dissolution rate of less than about 65% after about 4 hours following entry into a use environment. In some embodiments, the stable dosage form provides a dissolution rate of less than about 60% after about 4 hours following entry into a use environment. In some embodiments, the stable dosage form provides a dissolution rate of about 40% to about 80% after about 4 hours following entry into a use environment. In some embodiments, the stable dosage form provides a dissolution rate of about 45% to about 75% after about 4 hours following entry into a use environment. In some embodiments, the stable dosage form provides a dissolution rate of about 40% to about 70% after about 4 hours following entry into a use environment.

In some embodiments, the stable dosage form provides a dissolution rate (e.g., a single phase dissolution rate) of less than about 90% after about 6 hours following entry into a use environment. In some embodiments, the stable dosage form provides a dissolution rate of less than about 85% after about 6 hours following entry into a use environment. In some embodiments, the stable dosage form provides a dissolution rate of less than about 80% after about 6 hours following entry into a use environment. In some embodiments, the stable dosage form provides a dissolution rate of less than about 75% after about 6 hours following entry into a use environment. In some embodiments, the stable dosage form provides a dissolution rate of less than about 70% after about 6 hours following entry into a use environment. In some embodiments, the stable dosage form provides a dissolution rate of about 40% to about 95% after about 6 hours following entry into a use environment. In some embodiments, the stable dosage form provides a dissolution rate of about 50% to about 90% after about 6 hours following entry into a use environment. In some embodiments, the stable dosage form provides a dissolution rate of about 60% to about 85% after about 6 hours following entry into a use environment. In some embodiments, the stable dosage form provides a dissolution rate of about 60% to about 80% after about 6 hours following entry into a use environment.

In some embodiments, the stable dosage form provides a dissolution rate (e.g., a single phase dissolution rate) of less than about 95% after about 8 hours following entry into a use environment. In some embodiments, the stable dosage form provides a dissolution rate of less than about 90% after about 8 hours following entry into a use environment. In some embodiments, the stable dosage form provides a dissolution rate of less than about 85% after about 8 hours following entry into a use environment. In some embodiments, the stable dosage form provides a dissolution rate of about 65% to about 95% after about 8 hours following entry into a use environment. In some embodiments, the stable dosage form provides a dissolution rate of about 65% to about 90% after about 8 hours following entry into a use environment. In some embodiments, the stable dosage form provides a dissolution rate of about 65% to about 85% after about 8 hours following entry into a use environment. In some embodiments, the stable dosage form provides a dissolution rate of about 70% to about 85% after about 8 hours following entry into a use environment. In some embodiments, the stable dosage form provides a dissolution rate of about 70% to about 80% after about 8 hours following entry into a use environment.

In some embodiments, the stable dosage form provides a dissolution rate (e.g., a single phase dissolution rate) of less than about 95% after about 12 hours following entry into a use environment. In some embodiments, the stable dosage form provides a dissolution rate of less than about 90% after about 12 hours following entry into a use environment. In some embodiments, the stable dosage form provides a dissolution rate of about 75% to about 95% after about 12 hours following entry into a use environment. In some embodiments, the stable dosage form provides a dissolution rate of about 80% to about 95% after about 12 hours following entry into a use environment. In some embodiments, the stable dosage form provides a dissolution rate of about 80% to about 90% after about 12 hours following entry into a use environment.

In some embodiments, the stable dosage form provides a dissolution rate (e.g., a single phase dissolution rate) of at least about 80% (e.g., at least 80%) after about 6 hours to about 16 hours following entry into deionized water at a temperature of about 37° C. and subjected to USP apparatus II at 75 rpm (for example, after entry into 1000 mL of deionized water at a temperature of 37° C. and subjected to USP apparatus II at 75 rpm, wherein levomilnacipran is quantified using HPLC with a UV detector at a wavelength of 220 nm). In some embodiments, the stable dosage form provides a dissolution rate of at least about 80% after about 6 hours to about 12 hours following entry into deionized water at a temperature of about 37° C. and subjected to USP apparatus II at 75 rpm.

In some embodiments, the stable dosage form provides a dissolution rate (e.g., a single phase dissolution rate) of less than about 60% after about 2 hours following entry into deionized water at a temperature of about 37° C. and subjected to USP apparatus II at 75 rpm. In some embodiments, the stable dosage form provides a dissolution rate (e.g., a single phase dissolution rate) of less than about 55% after about 2 hours following entry into deionized water at a temperature of about 37° C. and subjected to USP apparatus II at 75 rpm. In some embodiments, the stable dosage form provides a dissolution rate of less than about 50% after about 2 hours following entry into deionized water at a temperature of about 37° C. and subjected to USP apparatus II at 75 rpm. In some embodiments, the stable dosage form provides a dissolution rate of less than about 45% after about 2 hours following entry into deionized water at a temperature of about 37° C. and subjected to USP apparatus II at 75 rpm. In some embodiments, the stable dosage form provides a dissolution rate of less than about 40% after about 2 hours following entry into deionized water at a temperature of about 37° C. and subjected to USP apparatus II at 75 rpm. In some embodiments, the stable dosage form provides a dissolution rate of about 20% to about 60% after about 2 hours following entry into deionized water at a temperature of about 37° C. and subjected to USP apparatus II at 75 rpm. In some embodiments, the stable dosage form provides a dissolution rate of about 25% to about 55% after about 2 hours following entry into deionized water at a temperature of about 37° C. and subjected to USP apparatus II at 75 rpm. In some embodiments, the stable dosage form provides a dissolution rate of about 30% to about 50% after about 2 hours following entry into deionized water at a temperature of about 37° C. and subjected to USP apparatus II at 75 rpm.

In some embodiments, the stable dosage form provides a dissolution rate (e.g., a single phase dissolution rate) of less than about 90% after about 4 hours following entry into deionized water at a temperature of about 37° C. and subjected to USP apparatus II at 75 rpm. In some embodiments, the stable dosage form provides a dissolution rate of less than about 80% after about 4 hours following entry into deionized water at a temperature of about 37° C. and subjected to USP apparatus II at 75 rpm. In some embodiments, the stable dosage form provides a dissolution rate of less than about 70% after about 4 hours following entry into deionized water at a temperature of about 37° C. and subjected to USP apparatus II at 75 rpm. In some embodiments, the stable dosage form provides a dissolution rate of less than about 65% after about 4 hours following entry into deionized water at a temperature of about 37° C. and subjected to USP apparatus II at 75 rpm. In some embodiments, the stable dosage form provides a dissolution rate of less than about 60% after about 4 hours following entry into deionized water at a temperature of about 37° C. and subjected to USP apparatus II at 75 rpm. In some embodiments, the stable dosage form provides a dissolution rate of about 40% to about 80% after about 4 hours following entry into deionized water at a temperature of about 37° C. and subjected to USP apparatus II at 75 rpm. In some embodiments, the stable dosage form provides a dissolution rate of about 45% to about 75% after about 4 hours following entry into deionized water at a temperature of about 37° C. and subjected to USP apparatus II at 75 rpm. In some embodiments, the stable dosage form provides a dissolution rate of about 40% to about 70% after about 4 hours following entry into deionized water at a temperature of about 37° C. and subjected to USP apparatus II at 75 rpm.

In some embodiments, the stable dosage form provides a dissolution rate (e.g., a single phase dissolution rate) of less than about 90% after about 6 hours following entry into deionized water at a temperature of about 37° C. and subjected to USP apparatus II at 75 rpm. In some embodiments, the stable dosage form provides a dissolution rate of less than about 85% after about 6 hours following entry into deionized water at a temperature of about 37° C. and subjected to USP apparatus II at 75 rpm. In some embodiments, the stable dosage form provides a dissolution rate of less than about 80% after about 6 hours following entry into deionized water at a temperature of about 37° C. and subjected to USP apparatus II at 75 rpm. In some embodiments, the stable dosage form provides a dissolution rate of less than about 75% after about 6 hours following entry into deionized water at a temperature of about 37° C. and subjected to USP apparatus II at 75 rpm. In some embodiments, the stable dosage form provides a dissolution rate of less than about 70% after about 6 hours following entry into deionized water at a temperature of about 37° C. and subjected to USP apparatus II at 75 rpm. In some embodiments, the stable dosage form provides a dissolution rate of about 40% to about 95% after about 6 hours following entry into deionized water at a temperature of about 37° C. and subjected to USP apparatus II at 75 rpm. In some embodiments, the stable dosage form provides a dissolution rate of about 50% to about 90% after about 6 hours following entry into deionized water at a temperature of about 37° C. and subjected to USP apparatus II at 75 rpm. In some embodiments, the stable dosage form provides a dissolution rate of about 60% to about 85% after about 6 hours following entry into deionized water at a temperature of about 37° C. and subjected to USP apparatus II at 75 rpm. In some embodiments, the stable dosage form provides a dissolution rate of about 60% to about 80% after about 6 hours following entry into deionized water at a temperature of about 37° C. and subjected to USP apparatus II at 75 rpm.

In some embodiments, the stable dosage form provides a dissolution rate (e.g., a single phase dissolution rate) of less than about 95% after about 8 hours following entry into deionized water at a temperature of about 37° C. and subjected to USP apparatus II at 75 rpm. In some embodiments, the stable dosage form provides a dissolution rate of less than about 90% after about 8 hours following entry into deionized water at a temperature of about 37° C. and subjected to USP apparatus II at 75 rpm. In some embodiments, the stable dosage form provides a dissolution rate of less than about 85% after about 8 hours following entry into deionized water at a temperature of about 37° C. and subjected to USP apparatus II at 75 rpm. In some embodiments, the stable dosage form provides a dissolution rate of about 65% to about 95% after about 8 hours following entry into deionized water at a temperature of about 37° C. and subjected to USP apparatus II at 75 rpm. In some embodiments, the stable dosage form provides a dissolution rate of about 65% to about 90% after about 8 hours following entry into deionized water at a temperature of about 37° C. and subjected to USP apparatus II at 75 rpm. In some embodiments, the stable dosage form provides a dissolution rate of about 65% to about 85% after about 8 hours following entry into deionized water at a temperature of about 37° C. and subjected to USP apparatus II at 75 rpm. In some embodiments, the stable dosage form provides a dissolution rate of about 70% to about 85% after about 8 hours following entry into deionized water at a temperature of about 37° C. and subjected to USP apparatus II at 75 rpm. In some embodiments, the stable dosage form provides a dissolution rate of about 70% to about 80% after about 8 hours following entry into deionized water at a temperature of about 37° C. and subjected to USP apparatus II at 75 rpm.

In some embodiments, the stable dosage form provides a dissolution rate (e.g., a single phase dissolution rate) of less than about 95% after about 12 hours following entry into deionized water at a temperature of about 37° C. and subjected to USP apparatus II at 75 rpm. In some embodiments, the stable dosage form provides a dissolution rate of less than about 90% after about 12 hours following entry into deionized water at a temperature of about 37° C. and subjected to USP apparatus II at 75 rpm. In some embodiments, the stable dosage form provides a dissolution rate of about 75% to about 95% after about 12 hours following entry into deionized water at a temperature of about 37° C. and subjected to USP apparatus II at 75 rpm. In some embodiments, the stable dosage form provides a dissolution rate of about 80% to about 95% after about 12 hours following entry into deionized water at a temperature of about 37° C. and subjected to USP apparatus II at 75 rpm. In some embodiments, the stable dosage form provides a dissolution rate of about 80% to about 90% after about 12 hours following entry into deionized water at a temperature of about 37° C. and subjected to USP apparatus II at 75 rpm.

In some embodiments, the stable dosage form of levomilnacipran achieves the discussed dissolution rates after storage of the dosage form for one, two, or even three months at 40° C. and 75% relative humidity (RH).

Pharmacokinetic (pK) Performance of the Stable Dosage Forms

The stable dosage forms provide sustained release of levomilnacipran over an extended period of time upon entering a use environment and are expected to achieve a desirable pK profile upon administration to human patients. In some embodiments, the stable dosage forms may provide (i.e., are expected to achieve) a therapeutic blood plasma level of levomilnacipran over approximately a twenty-four hour period, for example after single administration. For example, in some embodiments, the stable dosage forms may release levomilnacipran for about 4 hours to about 24 hours (e.g., for about 5 to about 24 hours, or even for about 6 hours to about 24 hours) following entry of the dosage form into a use environment.

In some embodiments, the stable dosage form may provide a mean Tmax (average time to maximum plasma concentration) of at least 1 hour following administration (e.g., single administration) to a patient. In some embodiments, the stable dosage form may provide a mean Tmax (average time to maximum plasma concentration) of at least 2 hours following administration (e.g., single administration) to a patient. In some embodiments, the stable dosage form may provide a mean Tmax (average time to maximum plasma concentration) of at least 3 hours following administration (e.g., single administration) to a patient. In some embodiments, the stable dosage form may provide a mean Tmax of at least 3.5 hours. Preferably, the stable dosage form of the present invention may provide a mean Tmax of at least 4 hours. For example, the stable dosage form may provide a mean Tmax of at least 4.5 hours.

In some embodiments, the dosage form may provide a mean Tmax of at least 5 hours. In some embodiments, the dosage form may provide a mean Tmax of at least 5.5 hours. In some embodiments, the dosage form may provide a mean Tmax of at least 6 hours. The stable dosage form can also provide a mean Tmax of about 4 hours to about 12 hours. For example, the stable dosage form can provide a mean Tmax of about 4 hours to about 10 hours. In some embodiments, the stable dosage form may provide a mean Tmax of about 4.5 hours to about 12 hours. In some embodiments, the dosage form may provide a mean Tmax of about 4.5 hours to about 10 hours. In some embodiments, the dosage form may provide a mean Tmax of about 5 hours to about 12 hours. In some embodiments, the dosage form may provide a mean Tmax of about 5 hours to about 10 hours. In some embodiments, the dosage form may provide a mean Tmax of about 4 hours to about 8 hours. In some embodiments, the dosage form may provide a mean Tmax of about 4.5 hours to about 8.5 hours. In some embodiments, the dosage form may provide a mean Tmax of about 5 hours to about 8 hours. In some embodiments, the dosage form may provide a mean Tmax of about 4 hours to about 9 hours.

In some embodiments, the stable dosage form may provide a mean $AUC0-\infty$ (plasma concentration of levomilnacipran over time) of about 500 to about 20,000 ng·hr/mL. In some embodiments, the stable dosage form may provide a mean $AUC0-\infty$ (plasma concentration of levomilnacipran over time) of about 500 to about 15,000 ng·hr/mL. In some embodiments, the stable dosage form may provide a mean $AUC0-\infty$ (plasma concentration of levomilnacipran over time) of about 500 to about 10,000 ng·hr/mL. In some embodiments, the stable dosage form may provide a mean $AUC0-\infty$ (plasma concentration of levomilnacipran over time) of about 1000 to about 9000 ng. In some embodiments, the stable dosage form may provide a mean $AUC0-\infty$ (plasma concentration of levomilnacipran over time) of about 500 to about 5,000 ng·hr/mL. In some embodiments, the stable dosage form may provide a mean $AUC0-\infty$ (plasma concentration of levomilnacipran over time) of about 500 to about 2500 ng·hr/mL. In some embodiments, the dosage form may provide a mean $AUC0-\infty$ of about 500 to about 2200 ng·hr/mL. In some embodiments, the dosage form may provide a mean $AUC0-\infty$ of about 700 to about 2500 ng·hr/mL.

In some embodiments, the dosage form may provide a mean $AUC0-\infty$ of about 700 to about 2200 ng·hr/mL. In some embodiments, the dosage form may provide a mean $AUC0-\infty$ of about 800 to about 2200 ng·hr/mL. In some embodiments, the dosage form may provide a mean $AUC0-\infty$ of about 700 to about 2300 ng·hr/mL. In some embodiments, the dosage form may provide a mean $AUC0-\infty$ of about 1000 to about 2000 ng·hr/mL. In some embodiments, the dosage form may provide a mean $AUC0-\infty$ of about 1000 to about 1800 ng·hr/mL. In some embodiments, the dosage form may provide a mean $AUC0-\infty$ of about 1100 to about 1800 ng·hr/mL. In some embodiments, the dosage form may provide a mean $AUC0-\infty$ of about 1200 to about 1700 ng·hr/mL. In some embodiments, the dosage form may provide a mean $AUC0-\infty$ of about 1300 to about 1700 ng·hr/mL. In some embodiments, the dosage form may provide a mean $AUC0-\infty$ of about 1300 to about 1650 ng·hr/mL.

The average maximum plasma concentration (Cmax) provided by the stable dosage forms can be modified (e.g., without substantially affecting the Tmax of the dosage form) by changing the strength of the dosage form. In some embodiments, the dosage form may provide a mean Cmax of less than about 200 ng/ml following administration (e.g., single administration) to a patient. In some embodiments, the dosage form may provide a mean Cmax of less than about 180 ng/ml. In some embodiments, the dosage form may provide a mean Cmax of less than about 170 ng/ml. In some embodiments, the dosage form may provide a mean Cmax of less than about 160 ng/ml. In some embodiments, the dosage form may provide a mean Cmax of less than about 150 ng/ml. In some embodiments, the dosage form may provide a mean Cmax of less than about 140 ng/ml. In some embodiments, the dosage form may provide a mean Cmax of less than about 130 ng/ml.

In some embodiments, the dosage form may provide a mean Cmax of less than about 120 ng/ml. In some embodiments, the dosage form may provide a mean Cmax of less than about 110 ng/ml. In some embodiments, the dosage form may provide a mean Cmax of less than about 100 ng/ml. In some embodiments, the dosage form may provide a mean Cmax between about 20 and about 250 ng/mL. In some embodiments, the dosage form may provide a mean Cmax between about 20 and about 200 ng/mL. In some embodiments, the dosage form may provide a mean Cmax between about 20 and about 180 ng/mL. In some embodiments, the dosage form may provide a mean Cmax between about 30 and about 140 ng/mL. In some embodiments, the dosage form may provide a mean Cmax between about 40 and about 140 ng/mL. In some embodiments, the dosage form may provide a mean Cmax between about 20 and about 150 ng/mL.

The stable dosage forms have also been found, in some embodiments, to provide a mean half life (T½) of at least about 6 hours. In some embodiments, the dosage form may provide a mean T½ of at least about 7 hours. In some embodiments, the dosage form may provide a mean T½ of at least about 8 hours. In some embodiments, the dosage form may provide a mean T½ of at least about 9 hours. In some embodiments, the dosage form may provide a mean T½ of at least about 10 hours. In some embodiments, the dosage form may provide a mean T½ of at least about 11 hours.

In some embodiments, the dosage form may provide a mean T½ of at least about 12 hours. In some embodiments, the dosage may provide a mean T½ of about 6 hours to about 24 hours. In some embodiments, the dosage may provide a mean T½ of about 6 hours to about 18 hours. In some embodiments, the dosage may provide a mean T½ of about 7 hours to about 18 hours. In some embodiments, the dosage may provide a mean T½ of about 8 hours to about 24 hours. In some embodiments, the dosage may provide a mean T½ of about 8 hours to about 18 hours.

In some preferred embodiments, the stable dosage form is a modified-release dosage form and provides a mean $AUC_{0-\infty}$ between about 1000 and about 9000 ng·hr/mL.

In some preferred embodiments, the stable dosage form is a modified-release dosage form and provides a mean Cmax between about 50 and about 350 ng/ml.

In some preferred embodiments, the stable dosage form is a modified-release dosage form and provides a mean Tmax between about 5 and 12 hours.

In some preferred embodiments, the stable dosage form is a modified-release dosage form and provides a mean T½ between about 9 hours and about 20 hours.

In some preferred embodiments, the stable dosage form is a modified-release dosage form and provides a mean $AUC_{0-\infty}$ between about 1000 and about 9000 ng·hr/mL, a mean Cmax between about 50 and about 350 ng/ml, a mean Tmax between about 5 and 12 hours, and a mean T½ between about 9 hours and about 20 hours.

In some embodiments, the stable dosage form may provide a mean Cmax of less than about 200 ng/ml, a mean $AUG_{0-\infty}$ of less than about 2500 ng·hr/mL and a mean Tmax of at least about 4 hours.

In some embodiments, the stable dosage form may provide a mean Cmax of less than about 180 ng/ml, a mean $AUG_{0-\infty}$ of less than about 2500 ng·hr/mL and a mean Tmax of at least about 4 hours.

In some embodiments, the stable dosage form may provide a mean Cmax of less than about 160 ng/ml, a mean $AUG_{0-\infty}$ of less than about 2500 ng·hr/mL and a mean Tmax of at least about 4 hours.

In some embodiments, the stable dosage form may provide a mean Cmax of less than about 150 ng/ml, a mean $AUG_{0-\infty}$ of less than about 2500 ng·hr/mL and a mean Tmax of at least about 4 hours.

In some embodiments, the stable dosage form may provide a mean Cmax of less than about 140 ng/ml, a mean $AUG_{0-\infty}$ of less than about 2500 ng·hr/mL and a mean Tmax of at least about 4 hours.

In some embodiments, the stable dosage form may provide a mean Cmax of less than about 140 ng/ml, a mean $AUG_{0-\infty}$ of less than about 2200 ng·hr/mL and a mean Tmax of at least about 4 hours.

In some embodiments, the stable dosage form may provide a mean Cmax of less than about 180 ng/ml, a mean $AUG_{0-\infty}$ of less than about 2200 ng·hr/mL and a mean Tmax of at least about 5 hours.

In some embodiments, the stable dosage form may provide a mean Cmax of less than about 180 ng/ml, a mean $AUG_{0-\infty}$ of less than about 2200 ng·hr/mL and a mean Tmax of at least about 6 hours.

In some embodiments, the stable dosage form may provide a mean Cmax of about 10 to about 200 ng/ml, a mean $AUG_{0-\infty}$ of about 500 to about 2500 ng·hr/mL and a mean Tmax between about 4 to about 10 hours.

In some embodiments, the stable dosage form may provide a mean Cmax of about 25 to about 175 ng/ml, a mean $AUG_{0-\infty}$ of about 500 to about 2500 ng·hr/mL and a mean Tmax between about 4 to about 10 hours.

In some embodiments, the stable dosage form may provide a mean Cmax of about 30 to about 150 ng/ml, a mean $AUC_{0-\infty}$ of about 500 to about 2500 ng·hr/mL and a mean Tmax between about 4 to about 10 hours.

In some embodiments, the stable dosage form may provide a mean Cmax of about 30 to about 120 ng/ml, a mean $AUC_{0-\infty}$ of about 500 to about 2500 hr/mL and a mean Tmax between about 4 to about 10 hours.

In some embodiments, the stable dosage form may provide a mean Cmax of about 10 to about 200 ng/ml, a mean $AUG_{0-\infty}$ of about 600 to about 2200 ng·hr/mL and a mean Tmax between about 4 to about 10 hours.

In some embodiments, the stable dosage form may provide a mean Cmax of about 10 to about 200 ng/ml, a mean $AUC_{0-\infty}$ of about 800 to about 2100 ng·hr/mL and a mean Tmax between about 4 to about 10 hours.

In some embodiments, the stable dosage form may provide a mean Cmax of about 10 to about 200 ng/ml, a mean $AUG_{0-\infty}$ of about 900 to about 2100 ng·hr/mL and a mean Tmax between about 4 to about 10 hours.

In some embodiments, the stable dosage form may provide a mean Cmax of about 30 to about 150 ng/ml, a mean $AUC_{0-\infty}$ of about 600 to about 2200 ng·hr/mL and a mean Tmax between about 4 to about 10 hours.

In some embodiments, the stable dosage form may provide a mean Cmax of about 30 to about 120 ng/ml, a mean $AUC_{0-\infty}$ of about 600 to about 2200 ng·hr/mL and a mean Tmax between about 4 to about 10 hours.

In some embodiments, the stable dosage form may provide an in vivo plasma profile with a mean Cmax of about 10 to about 200 ng/ml, a mean $AUG_{0-\infty}$ of about 500 to about 2500 ng·hr/mL and a mean Tmax between about 4 to about 8 hours.

In some embodiments, the stable dosage form may provide an in vivo plasma profile with a mean Cmax of about 10 to about 200 ng/ml, a mean $AUG_{0-\infty}$ of about 500 to about 2500 ng·hr/mL and a mean Tmax between about 5 to about 8 hours.

In some embodiments, the stable dosage form may provide an in vivo plasma profile with a mean Cmax of about 25 to about 175 ng/ml, a mean $AUG_{0-\infty}$ of about 600 to about 2200 ng·hr/mL and a mean Tmax between about 4 to about 9 hours.

In some embodiments, the stable dosage form may provide an in vivo plasma profile with a mean Cmax of about 30 to about 150 ng/ml, a mean $AUG_{0-\infty}$ of about 800 to about 2100 ng·hr/mL and a mean Tmax between about 4 to about 9 hours.

In some embodiments, a dosage form is provided, wherein the dosage form may provide an in vivo plasma profile with a mean Cmax of less than about 125 ng/ml, a mean $AUC_{0-\infty}$ of less than about 1000 to about 2200 ng·hr/mL and a mean Tmax of at least about 4 hours.

Methods of Treatment Using the Stable Dosage Forms

The present invention also provides methods for treating a disease, disorder or condition that can be managed by inhibition (e.g., double inhibition and/or selective inhibition) of 5-HT and NE reuptake, for example, anxiety disorders or depression (e.g., major depressive disorder (MDD)) in a mammal (e.g., human) by administering the stable dosage form to a patient in need thereof.

In some embodiments, a method is provided for treating or preventing depression (e.g., atypical depression or MDD), anxiety (e.g., generalized anxiety disorder) or fatigue associated with depression or anxiety in a patient in need thereof by administering the stable dosage form of levomilnacipran to said patient. In some embodiments, a method is provided for treating or preventing major depressive disorder (MDD) (e.g., acute MDD or atypical MDD) in a patient in need thereof by administering the stable dosage form of levomilnacipran to said patient. In some embodiments, a method is provided for treating or preventing MDD with unresolved, concomitant or accompanying fatigue in a patient in need thereof by administering the stable dosage form of levomilnacipran to said patient.

In some embodiments, the stable dosage form of levomilnacipran is used to treat or prevent relapse of MDD in a patient in need thereof by administering the dosage form to said patient. In some embodiments, the stable dosage form is used to treat or prevent fatigue (e.g., fatigue associated with MDD or other form of depression) in a patient in need thereof by administering the dosage form to said patient. In some embodiments, the stable dosage form is used to treat or prevent sexual dysfunction (e.g., erectile dysfunction) in a patient in need thereof by administering the dosage form to said patient. In some embodiments, the stable dosage form is used to treat or prevent pain associated with depression (e.g., MDD) in a patient in need thereof by administering the dosage form to said patient.

In some embodiments, the stable dosage form of the present invention is used to treat or prevent melancholia, dysthymia, somnolence, cognitive impairment, sleep disorders and/or hyperlipidemia associated (or concomitant) with depression (e.g., MDD) in a patient in need thereof by administering the stable dosage form to said patient.

In some embodiments, a method is provided for treating or preventing neuropathic pain (e.g., diabetic polyneuropathic pain (DPNP)) in a patient in need thereof, wherein the method comprises administering an effective amount of the stable dosage form of levomilnacipran to the patient.

Through administration of the stable dosage form of levomilnacipran, there is provided a method for obtaining a flattened drug plasma concentration to time profile, thereby affording a tighter plasma therapeutic range control than can be obtained with multiple daily dosing. In other words, a method is provided for eliminating the sharp peaks and troughs in blood plasma drug levels induced by multiple daily dosing with conventional immediate release formulations of levomilnacipran. In essence, the plasma levels of levomilnacipran rise after administration of the stable dosage forms of this invention for several hours and then begin to fall through a protracted, substantially linear decrease from the peak plasma level for the remainder of an approximately twenty-four hour period, maintaining at least a threshold therapeutic level of levomilnacipran during the entire period.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Example 1

Preparation of a Dosage Form of Levomilnacipran

Beads of levomilnacipran were prepared by preheating sugar spheres (approximately 30-35 mesh) and layering the preheated sugar spheres with a drug layer solution for about 3.5 hours via a Wurster process to form drug-loaded beads. The drug layer solution included levomilnacipran, Povidone K30, talc and a dehydrated alcohol. The drug-loaded beads were dried in the fluid bed for about 30 minutes and sieved to yield immediate-release levomilnacipran beads (approx. 540 mg/g) which comprised approximately the concentrations of components shown in Table 4:

TABLE 4

| Components | Formulation | |
|---|---|---|
| | % w/w | kg/Batch |
| Levomilnacipran | 54 | 30 |
| Sugar Spheres | 37 | 20 |
| Povidone K30 | 6 | 3 |
| Talc | 3 | 2 |
| Dehydrated alcohol[1] | — | — |
| Total | 100 | 55 |

[1]Eliminated during the manufacturing process

The levomilnacipran beads were then preheated and coated with a dispersion solution via a Wurster process. The dispersion solution comprised ethyl cellulose N22, triethyl citrate, talc and a dehydrated alcohol. The coated beads were carefully cured in the fluid bed and screened to yield sustained release beads of levomilnacipran (approx. 460 mg/g) prior to filling into capsules. The sustained release levomilnacipran beads comprised approximately the concentrations of components shown in Table 5:

TABLE 5

| Components | Formulation | |
|---|---|---|
| | % w/w | kg/Batch |
| Levomilnacipran Beads | 85 | 51 |
| Ethyl cellulose N22 | 10 | 6 |
| Triethyl citrate | 2 | 1.2 |
| Talc | 3 | 1.8 |
| Dehydrated alcohol[1] | q.s. | q.s. |
| Total | 100 | 60 |

[1]Eliminated during the manufacturing process

Example 2

Stability of the Dosage Form Prepared in Example 1

The stability of the dosage form of levomilnacipran prepared in Example 1 was assessed following storage of the dosage form in two different types of capsules (namely, hard gelatin capsules and HPMC capsules) for three months at 40° C. and 75% relative humidity (RH).

Table 6 shows the approximate concentrations of impurities that were found within the hard gelatin capsules of the stable dosage form of levomilnacipran following three months of storage.

TABLE 6

| Impurities | Concentration |
|---|---|
| (1S,5R)1-phenyl-3-azabicyclo[3-1-0]-hexane-2-one | Approx. 0.06% |
| Total unknown related substances | Less than appox. 0.05% |
| Total all related substances | Approx. 0.06% |

Table 7 shows the approximate concentrations of impurities that were found within HPMC capsules of the stable dosage form of levomilnacipran.

TABLE 7

| Impurities | Concentration |
|---|---|
| (1S,5R)1-phenyl-3-azabicyclo[3-1-0]-hexane-2-one | Less than approx. 0.05% |
| Total unknown related substances | Less than approx. 0.05% |
| Total all related substances | Less than 0.05% |

Example 3

Dissolution Rates of Dosage Form Prepared in Example 1

The dissolution rates of the stable dosage form of levomilnacipran prepared in Example 1 was evaluated in 1000 mL of deionized water at 37° C. using USP apparatus II at 75 rpm. Quantification of levomilnacipran was determined using with a UV detector at a wavelength of 220 nm.

The dissolution profile of the stable dosage form prepared in Example 1 (and loaded into an HPMC capsule containing no desiccant) is shown in FIG. 1 and in Table 8.

The dissolution profile of the stable dosage form prepared in Example 1 was also determined after storing the dosage form for one, two and three months at 40° C. and 75% relative humidity (RH), wherein the dosage form was loaded into HPMC capsules (containing 1 gram or no desiccant), as is shown in Table 8 and in FIGS. 1-5.

Figure 2:
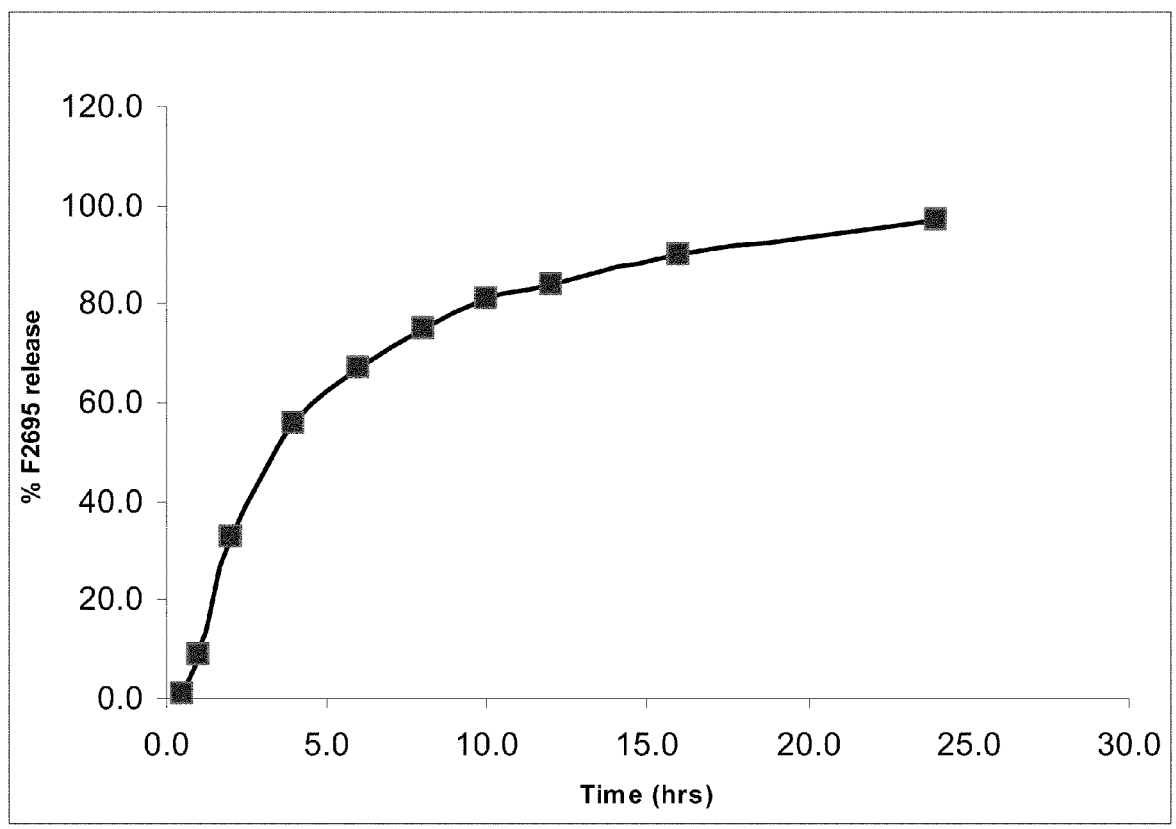
FIG. 2 show the dissolution rates for a stable dosage form of levomilnacipran in accordance with an embodiment of the present invention following one month of storage at 40° C. and 75% relative humidity (RH).
Figure 3:
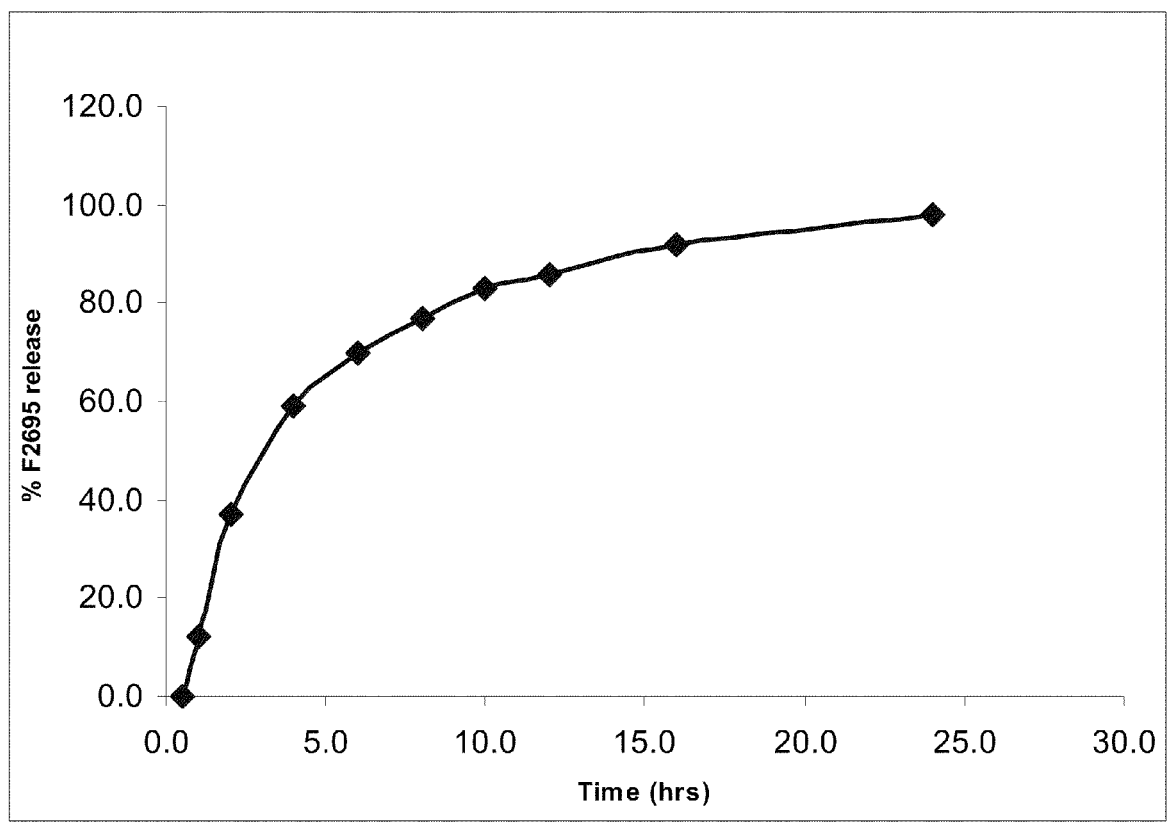
FIG. 3 show the dissolution rates for a stable dosage form of levomilnacipran in accordance with an embodiment of the present invention following two months of storage at 40° C. and 75% RH.
Figure 4:
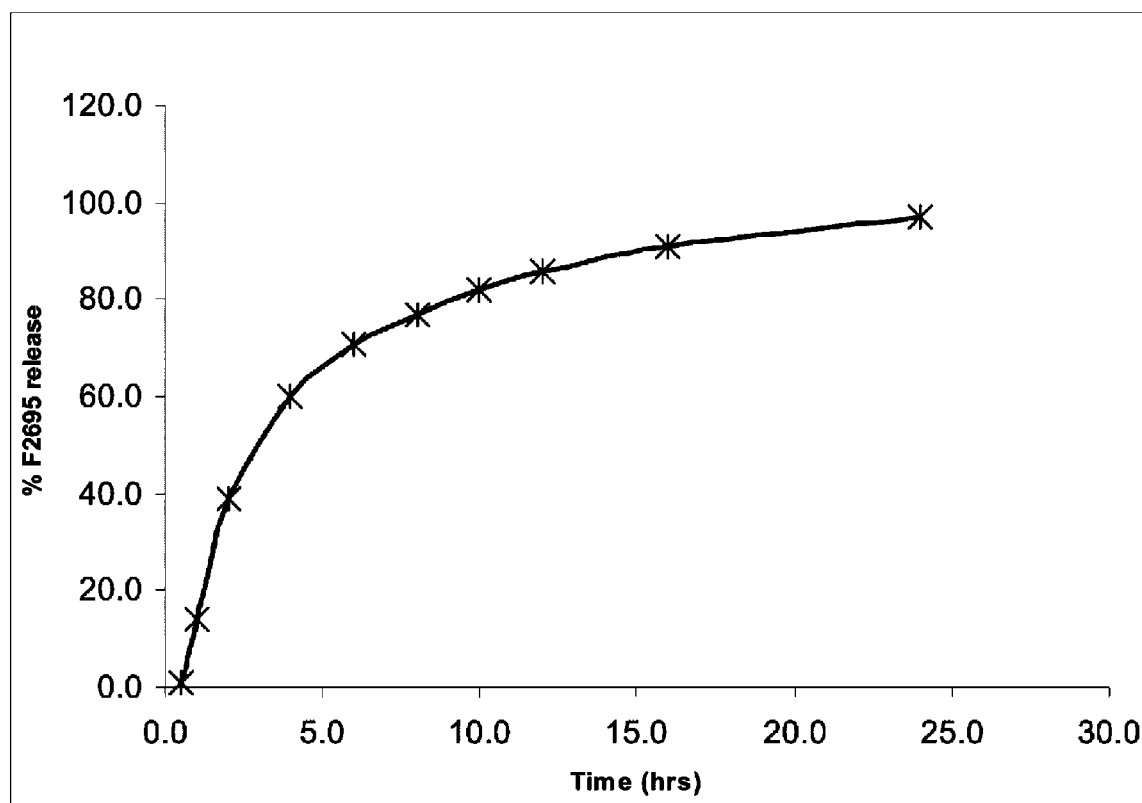
FIG. 4 show the dissolution rates for a stable dosage form of levomilnacipran in accordance with an embodiment of the present invention following three months of storage at 40° C. and 75% RH.
Figure 5:
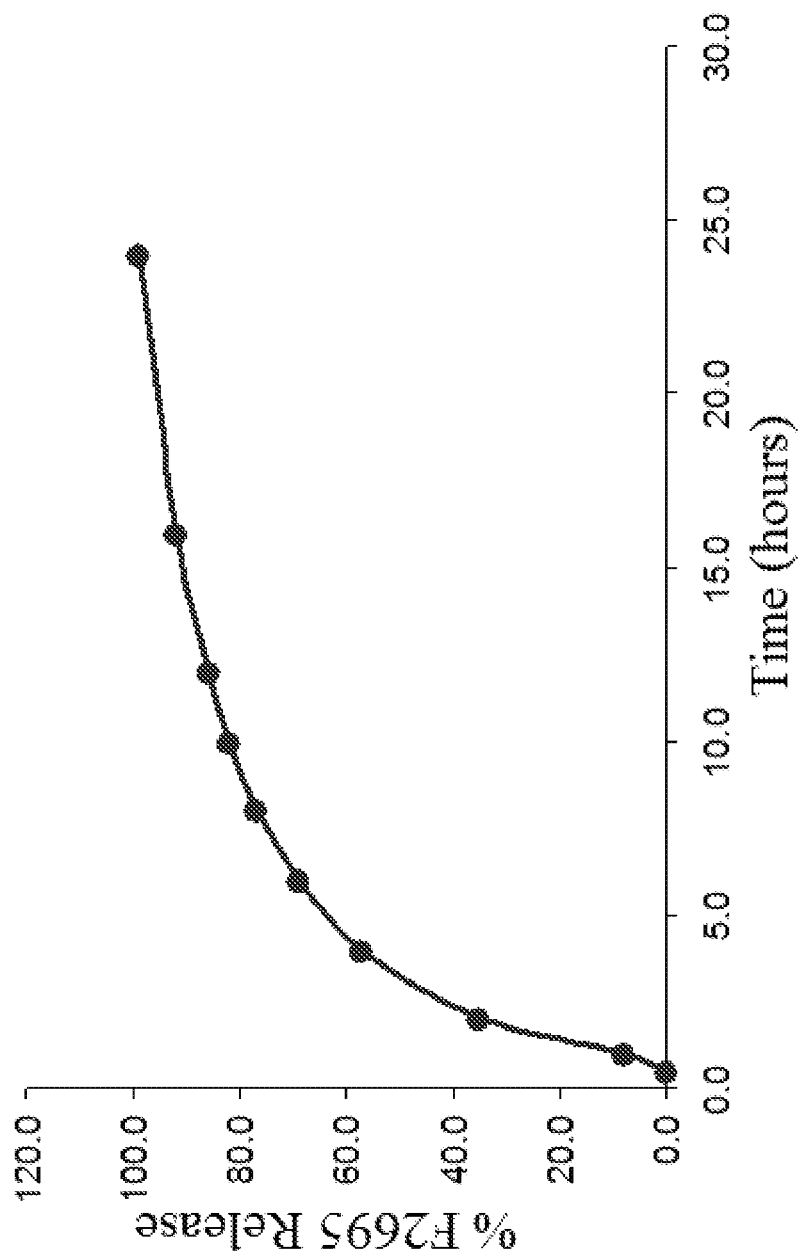
FIG. 5 show the dissolution rates for a stable dosage form of levomilnacipran in accordance with an embodiment of the present invention following three months of storage at 40° C. and 75% RH wherein the dosage form contained 1 gram of desiccant.

In particular, FIG. 1 shows the dissolution rate for the stable dosage form of levomilnacipran after no storage, wherein the dosage form is loaded into an HPMC capsule that contains no desiccant. FIG. 2 shows the dissolution rate for the stable dosage form of levomilnacipran after 1 month of storage at 40° C. and 75% RH, wherein the dosage form is loaded into an HPMC capsule that contains no desiccant. FIG. 3 shows the dissolution rate for the stable dosage form of levomilnacipran after 2 months of storage at 40° C. and 75% RH, wherein the dosage form is loaded into an HPMC capsule that contains no desiccant. FIG. 4 shows the dissolution rate for the stable dosage form of levomilnacipran after 3 months of storage at 40° C. and 75% RH, wherein the dosage form is loaded into an HPMC capsule that contains no desiccant. FIG. 5 shows the dissolution rate for the stable dosage form of levomilnacipran after 3 months of storage at 40° C. and 75% RH, wherein the dosage form is loaded into an HPMC capsule that contains 1 gram of desiccant.

TABLE 8

| Time (hrs) | Initial (no desiccant) Average % Release | 1 month storage (no desiccant) Average % Release | 2 months storage (no desiccant) Average % Release | 3 months storage (no desiccant) Average % Release | 3 months storage (1 g desiccant) Average % Release |
|---|---|---|---|---|---|
| 0.5 | 0 | 1 | 0 | 1 | 0 |
| 1.0 | 5 | 9 | 12 | 14 | 8 |
| 2.0 | 31 | 33 | 37 | 39 | 35 |
| 4.0 | 56 | 56 | 59 | 60 | 57 |
| 6.0 | 68 | 67 | 70 | 71 | 69 |
| 8.0 | 76 | 75 | 77 | 77 | 77 |
| 10.0 | 82 | 81 | 83 | 82 | 82 |
| 12.0 | 86 | 84 | 86 | 86 | 86 |
| 16.0 | 92 | 90 | 92 | 91 | 92 |
| 24.0 | 98 | 97 | 98 | 97 | 99 |

Example 4

X-Ray Powder Diffractometry (XRD) Analysis of an Active Ingredient Comprising Substantially Pure Levomilnacipran A sample of an active ingredient comprising at least 98% by weight of levomilnacipran hydrochloride was loaded onto a deep aluminum holder and exposed to CuKα radiation (40 kV×40 mA) in a wide-angle bench-top X-ray diffractometer (Model D8, Bruker AXS Inc., Madison Wis.). The instrument was operated in the step-scan mode in increments of 0.05°2θ. The angular range was 5 to 40°2θ, and the scan rate was 0.15°2θ/min. The data collection and analyses were performed with commercially available software.

Figure 6:
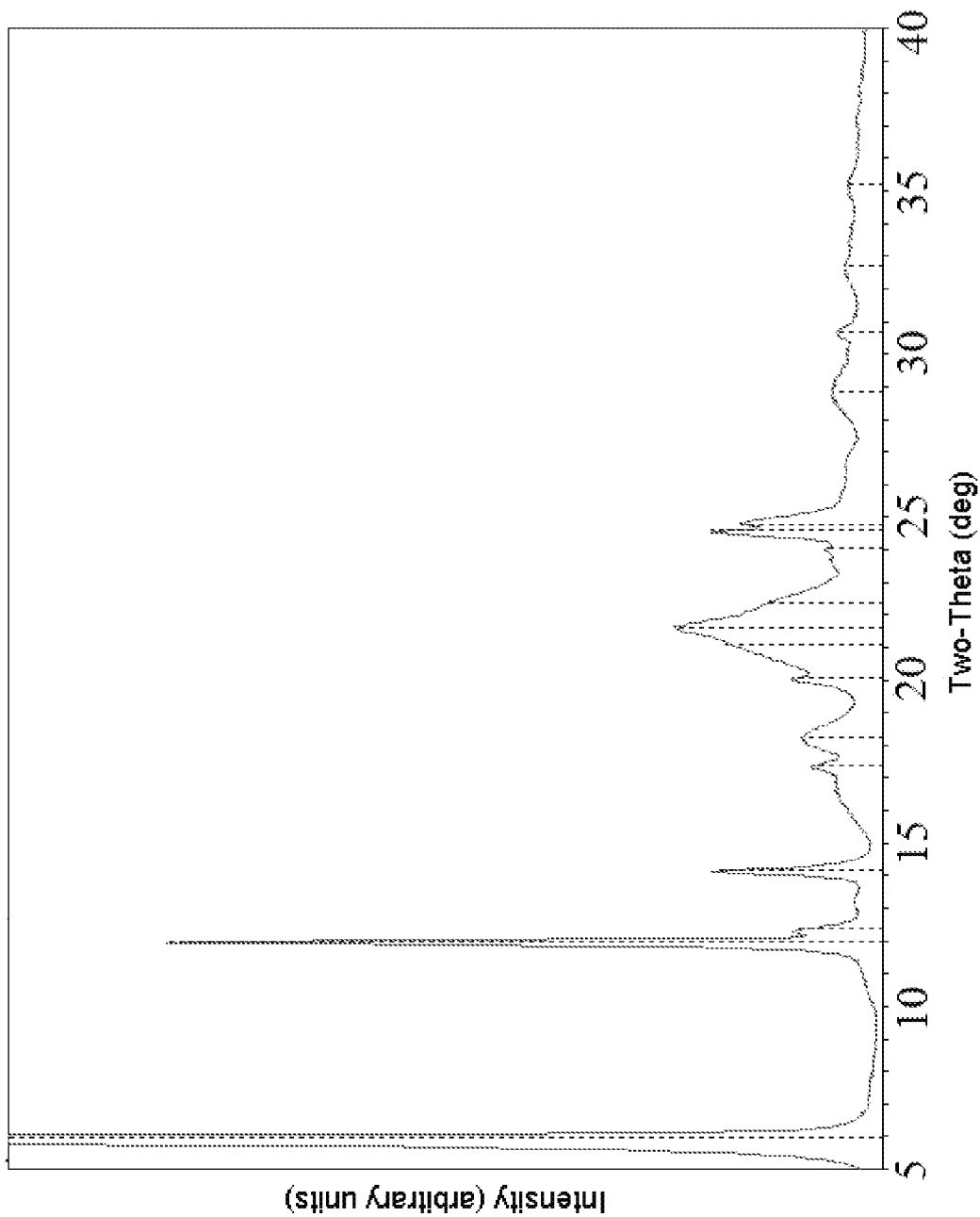
FIG. 6 shows an X-ray powder diffraction pattern (XRD) for an active pharmaceutical ingredient comprising substantially pure levomilnacipran.

Peak positions for the XRD pattern in FIG. 6 are provided in Table 1.

TABLE 1

| 2-Theta | d (Å) |
|---|---|
| 6.0 | 14.8 |
| 12.0 | 7.4 |
| 12.4 | 7.1 |
| 14.2 | 6.2 |
| 17.4 | 5.1 |
| 18.2 | 4.9 |
| 20.1 | 4.4 |

TABLE 1-continued

| 2-Theta | d (Å) |
|---|---|
| 21.1 | 4.2 |
| 21.6 | 4.1 |
| 22.4 | 4.0 |
| 24.1 | 3.7 |
| 24.6 | 3.6 |
| 24.8 | 3.6 |
| 28.8 | 3.1 |
| 30.7 | 2.9 |
| 32.7 | 2.7 |
| 35.2 | 2.5 |

Example 5

X-Ray Powder Diffractometry (XRD) Analysis of the Immediate-Release Levomilnacipran Beads Prepared in Example 1

IR Levomilnacipran beads prepared in Example 1 were loaded onto a deep aluminum holder and exposed to CuKα radiation (40 kV×40 mA) in a wide-angle bench-top X-ray diffractometer (Model D8, Bruker AXS Inc., Madison Wis.). The instrument was operated in the step-scan mode in increments of 0.05°2θ. The angular range was 5 to 40°2θ, and the scan rate was 0.15°2θ/min. The data collection and analyses were performed with commercially available software.

Figure 7:
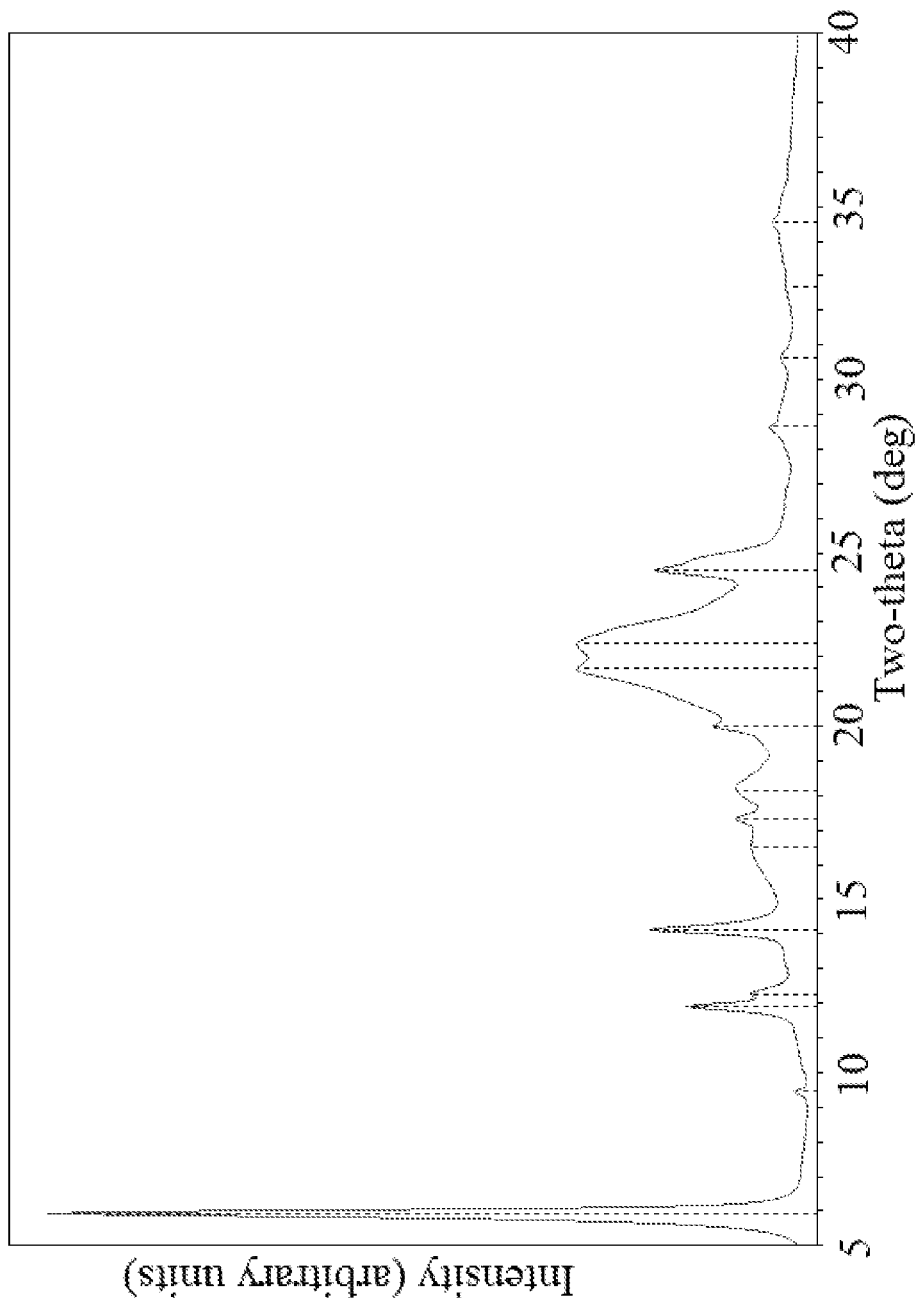
FIG. 7 shows an XRD of a stable immediate-release dosage form of levomilnacipran in accordance with an embodiment of the invention.

Peak positions for the XRD pattern in FIG. 7 are provided in Table 2.

TABLE 2

| 2-Theta | d (Å) |
|---|---|
| 2.3 | 39.2 |
| 5.9 | 14.9 |
| 9.5 | 9.3 |
| 11.9 | 7.4 |
| 12.3 | 7.2 |
| 14.1 | 6.3 |
| 16.5 | 5.4 |
| 17.3 | 5.1 |
| 18.1 | 4.9 |
| 20.0 | 4.4 |
| 21.7 | 4.1 |
| 22.4 | 4.0 |
| 24.5 | 3.6 |
| 28.6 | 3.1 |
| 30.6 | 2.9 |
| 32.7 | 2.7 |
| 34.5 | 2.6 |

Example 6

X-Ray Powder Diffractometry (XRD) Analysis of the Sustained-Release Dosage Form Prepared in Example 1

A small amount of the sustained-release dosage form prepared in Example 1 was loaded on a deep aluminum holder and exposed to CuKα radiation (40 kV×40 mA) in a wide-angle bench-top X-ray diffractometer (Model D8, Bruker AXS Inc., Madison Wis.). The instrument was operated in a step-scan mode in increments of 0.05°2θ. The angular range was 5 to 40°2θ, and the scan rate was 0.15°2θ/min. Data collection and analyses were performed with commercially available software (specifically, DIFFRACplus XRD Commander, Bruker-AXS GmbH; and JADE, Materials Data, Inc.).

Figure 8:
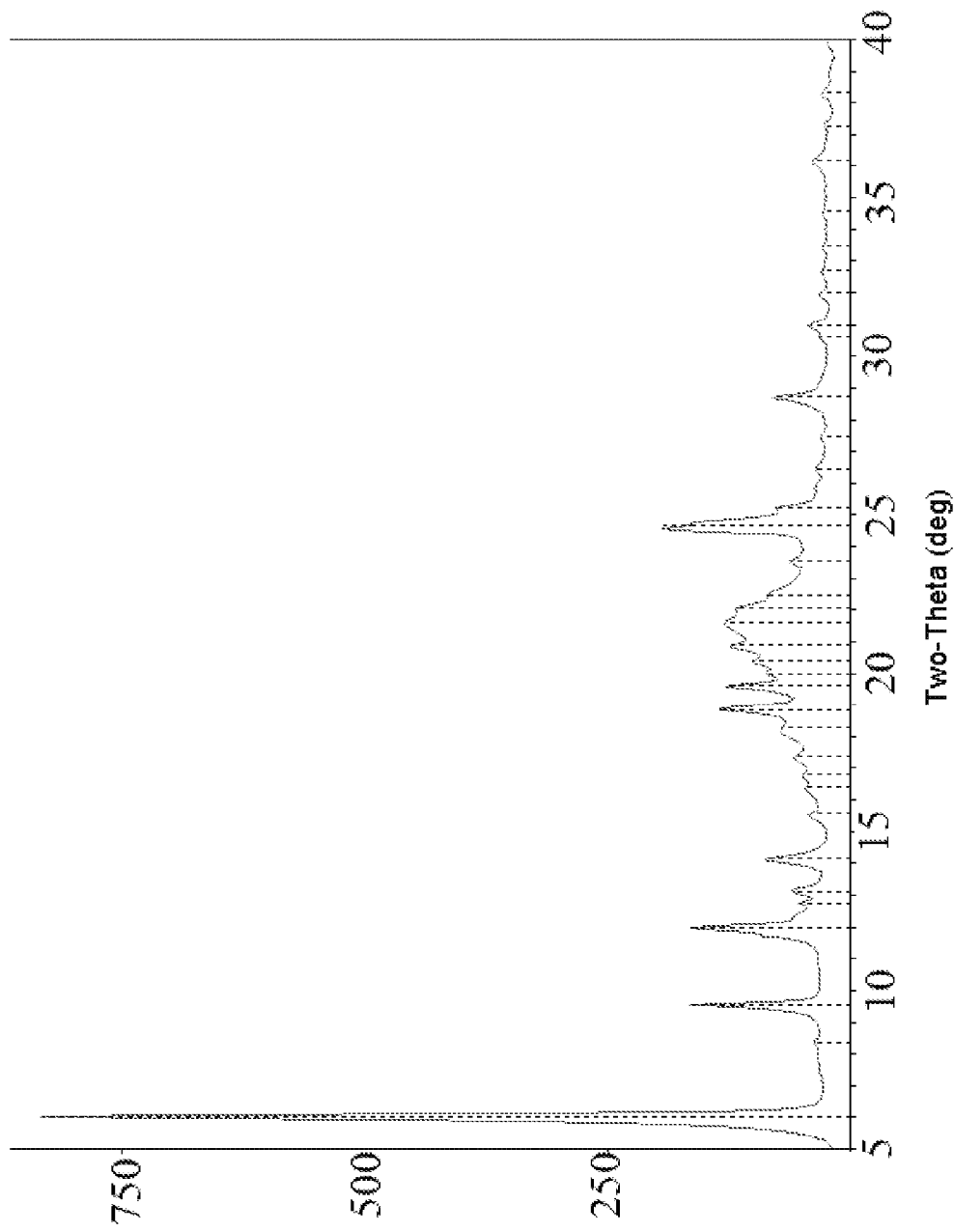
FIG. 8 shows an XRD of a stable sustained-release dosage form of levomilnacipran in accordance with an embodiment of the invention.

The XRD pattern for the stable dosage form of levomilnacipran is shown in FIG. 7. Peak positions for the XRD pattern in FIG. 8 are provided in Table 3.

TABLE 3

| 2-Theta | d (Å) |
|---|---|
| 6.0 | 14.7 |
| 8.3 | 10.6 |
| 9.6 | 9.2 |
| 12.0 | 7.4 |
| 12.8 | 6.9 |
| 13.1 | 6.7 |
| 14.2 | 6.2 |
| 15.6 | 5.7 |
| 16.4 | 5.4 |
| 16.8 | 5.3 |
| 17.4 | 5.1 |
| 18.3 | 4.8 |
| 18.9 | 4.7 |
| 19.6 | 4.5 |
| 20.0 | 4.4 |
| 20.4 | 4.4 |
| 20.9 | 4.2 |
| 21.6 | 4.1 |
| 22.1 | 4.0 |
| 22.5 | 4.0 |
| 23.6 | 3.8 |
| 24.7 | 3.6 |
| 25.2 | 3.5 |
| 26.4 | 3.4 |
| 27.5 | 3.2 |
| 28.7 | 3.1 |
| 30.6 | 2.9 |
| 31.0 | 2.9 |
| 32.0 | 2.8 |
| 32.7 | 2.7 |
| 33.5 | 2.7 |
| 34.6 | 2.6 |
| 36.2 | 2.5 |
| 37.3 | 2.4 |
| 38.3 | 2.3 |

Example 7

Administration of Stable Dosage Forms of Levomilnacipran to Human Patients (Prophetic)

The stable dosage forms of levomilnacipran of the present invention can be administered to human patients in the form of capsules that contain 50 mg of levomilnacipran. The capsules may contain microgranules that are coated with about 7.5 wt. % of ethyl cellulose (EC) ("dosage form 1"), about 10 wt. % EC ("dosage form 2") and about 12.5 wt. % EC ("dosage form 3").

Dosage forms 1-3 can be administered to patients after a fasting period of at least about 10 hours. Blood samples can be collected from each patient before administration and at several time points after administration (e.g., at 30 minutes, 1 hour, 2 hours, 3 hours, 4 hours, 5 hours, 6 hours, 7 hours, 8 hours, 10 hours, 12 hours, 24 hours, 48 hours and 72 hours). Plasma samples from each patient can be assayed for levomilnacipran quantification using a validated on-line extraction method (Turbulent Flow Chromatography) coupled with LC/MS-MS detection.

Oral administration of the stable dosage form is expected to yield pharmacokinetic (pK) parameters substantially as shown for any of dosage forms 1-3 in Table 9. In some preferred embodiments, the stable dosage form will yield pK parameters substantially as shown for dosage form 2. These pK parameters are expressed as geometric mean (geometric CV %) and [range].

TABLE 9

| Dosage Form | Cmax (ng·mL$^{-1}$) | Tmax* (h) | AUC$_{0-\infty}$ (h·ng·mL$^{-1}$) | T½ (h) | Tlag* (h) | F (%) |
|---|---|---|---|---|---|---|
| 1 | 83 (23%) [53-120] | 5 [5-7] | 1585 (19%) [1035-2018] | 12 (11%) [10-15] | 0.3 [0-0.5] | 107 (5%) [96-113] |
| 2 | 70 (25%) [43-97] | 6 [5-7] | 1477 (17%) [1032-1825] | 13 (13%) [10-15] | 0.5 [0-1] | 100 (11%) [82-114] |
| 3 | 58 (16%) [42.5-75] | 7 [5-8] | 1331 (15%) [967-1592] | 13 (14%) [10-16.5] | 1 [0-1] | 89 (9%) [73-100] |

*Median value for Tmax and Tlag.

Figure 9:
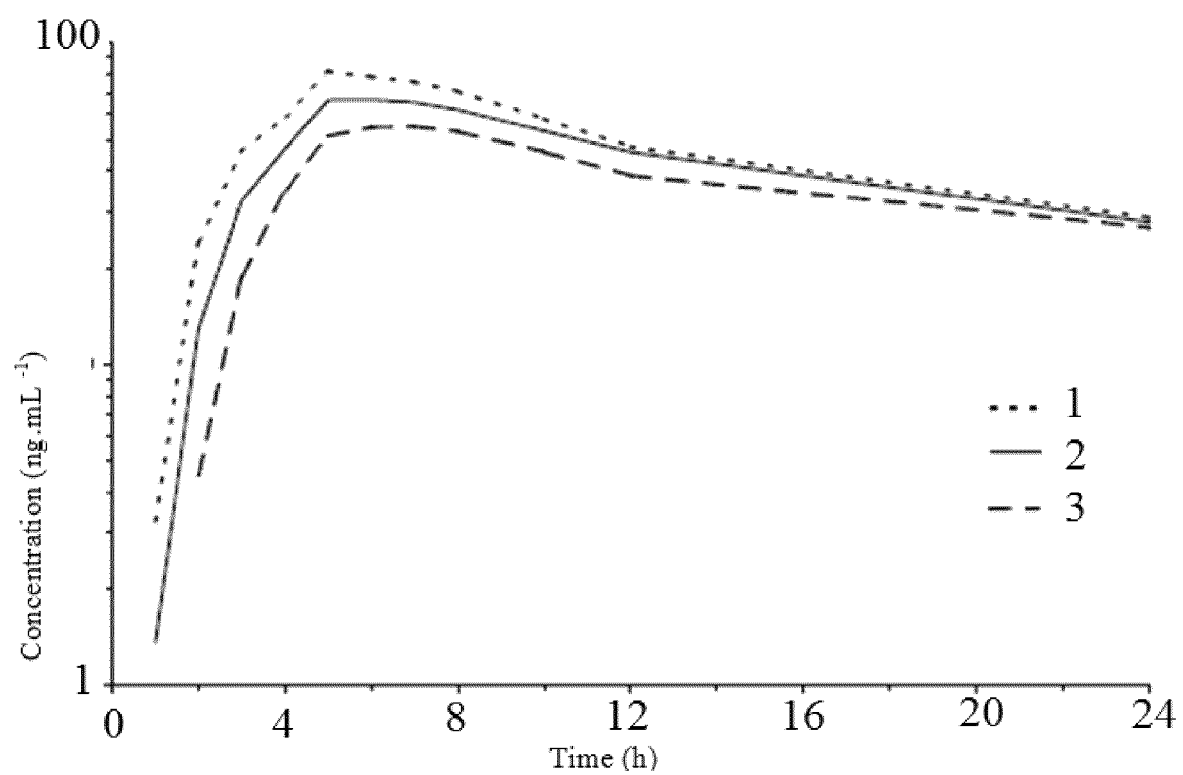
FIG. 9 shows the mean plasma concentration of levomilnacipran versus time that may be achieved via single administration of Stable dosage forms of levomilnacipran to human patients.

The mean levomilnacipran plasma concentration versus time profiles that may be obtained after single oral administrations (up to 24 hours post dosing) are shown in FIG. 9 (log-linear scale expressed as geometric mean).

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure.

The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A method for treating major depressive disorder in a patient in need thereof, comprising administering to the patient about 120 mg/day of levomilnacipran or a pharmaceutically acceptable salt thereof in one or more sustained release oral dosage forms,
   wherein the administering step provides a therapeutic blood plasma level of levomilnacipran or pharmaceutically acceptable salt thereof over approximately a twenty-four hour period to treat major depressive disorder in the patient, and
   wherein the administering step provides an average maximum plasma concentration ($C_{max}$) between about 50 ng/mL and about 350 ng/mL of levomilnacipran or pharmaceutically acceptable salt thereof, an $AUC_{0-\infty}$ between about 1000 ng·hr/mL and about 9000 ng·hr/mL and a $T_{max}$ of at least 3 hours to the patient.

2. The method of claim 1, wherein the administering step comprises administering levomilnacipran hydrochloride.

3. The method of claim 1, wherein the administering step provides a mean $T_{max}$ between about 4 hours and about 10 hours to the patient.

4. The method of claim 1, wherein the administering step provides a mean $T_{max}$ of at least 3 hours and a mean $AUC_{0-\infty}$ between about 5000 ng·hr/mL and about 9000 ng·hr/mL to the patient.

5. The method of claim 1, wherein the administering step provides a mean $T_{max}$ of at least 3 hours and a mean $AUG_{0-\infty}$ within ten percent of 5000 ng·hr/mL to the patient.

6. The method of claim 1, wherein the administering step provides a mean $T_{max}$ of at least 3 hours and a mean $AUG_{0-\infty}$ within twenty percent of 5000 ng·hr/mL to the patient.

7. The method of claim 1, wherein the administering step further comprises administering within the sustained-release oral dosage forms between about 0.001% and about 0.5% by weight of (1S,5R) 1-phenyl-3-azabicyclo[3-1-0]hexane-2-one relative to the amount of levomilnacipran or salt thereof.

8. The method of claim 1, wherein the administering step further comprises administering within the sustained-release oral dosage forms between about 0.001% and about 0.2% by weight of (1S,5R) 1-phenyl-3-azabicyclo[3-1-0]hexane-2-one relative to the amount of levomilnacipran or salt thereof.

* * * * *